(12) United States Patent
Hendon et al.

(10) Patent No.: US 12,072,283 B2
(45) Date of Patent: Aug. 27, 2024

(54) SYSTEM, METHOD, COMPUTER-ACCESSIBLE AND APPARATUS FOR PROVIDING NEAR-INFRARED SPECTROSCOPY FOR ANATOMICAL MAPPING OF THE EPICARDIUM

(71) Applicant: The Trustees of Columbia University in the City of New York, New York, NY (US)

(72) Inventors: Christine Hendon, Bronx, NY (US); Rajinder Singh-Moon, Mastic, NY (US); James McLean, New York, NY (US); Soo Young Park, Seoul (KR)

(73) Assignee: The Trustees of Columbia University in the City of New York, New York, NY (US)

( * ) Notice: Subject to any disclaimer, the term of this patent is extended or adjusted under 35 U.S.C. 154(b) by 833 days.

(21) Appl. No.: 16/906,429

(22) Filed: Jun. 19, 2020

(65) Prior Publication Data
US 2021/0396661 A1 Dec. 23, 2021

(51) Int. Cl.
| | | |
|---|---|---|
| *G01N 21/3563* | (2014.01) | |
| *A61B 5/00* | (2006.01) | |
| *A61B 18/00* | (2006.01) | |
| *A61B 18/14* | (2006.01) | |
| *G01N 21/359* | (2014.01) | |
| *G01N 21/47* | (2006.01) | |

(52) U.S. Cl.
CPC ....... *G01N 21/3563* (2013.01); *A61B 5/0075* (2013.01); *A61B 5/0086* (2013.01); *A61B 18/1492* (2013.01); *G01N 21/359* (2013.01); *G01N 21/474* (2013.01); *A61B 2018/00577* (2013.01); *G01N 2021/4709* (2013.01); *G01N 2021/4745* (2013.01)

(58) Field of Classification Search
CPC ............... A61B 5/0075; A61B 5/0086; A61B 5/0066; A61B 18/1492; G01N 21/3563; G01N 21/269; G01N 21/474
See application file for complete search history.

(56) References Cited

PUBLICATIONS

Singh-Moon et al. "Near-Infrared Spectroscopy Integrated Catheter for Characterization of Myocardial Tissues: Preliminary Demonstrations to Radiofrequency Ablation Therapy for Atrial Fibrillation", Biomedical Optics Express, 2015, vol. 6, No. 7, p. 2494-2511. (Year: 2015).*

(Continued)

*Primary Examiner* — David P Porta
*Assistant Examiner* — Casey Bryant
(74) *Attorney, Agent, or Firm* — HUNTON ANDREWS KURTH LLP

(57) ABSTRACT

An exemplary catheter can be provided, which can include, for example a source fiber(s) configured to (i) receive a near infrared spectroscopic (NIRS) radiation, and (ii) provide the NIRS radiation to a portion(s) of a sample(s), a detection fiber(s) configured to receive a return radiation from the sample(s) that can be based on the NIRS radiation that was provided to the portion(s) of the sample(s), and an ablation electrode(s) configured to ablate the sample(s) based on the return radiation. The source fiber(s), the detection fiber(s), and the ablation electrode(s) can be integrated into the single sheath. The ablation electrode(s) can be a radiofrequency ablation electrode.

27 Claims, 21 Drawing Sheets

(56) References Cited

PUBLICATIONS

Meglan et al. "Techniques for Avoidance of Coronary Vasculature during Epicardial Needle Insertions with a Miniature Robotic Walker", ICMRE 2017: Proceedings of the 3rd International Conference on Mechatronics and Robotics Engineering, Feb. 2017, pp. 1-5. (Year: 2017).*

Meglan et al., "Techniques for epicardial mapping and ablation with a miniature robotic walker", Robotic Surgery: Research and Reviews 2017:4 25-31 (Year: 2017).*

Sosa E, Scanavacca M, d'Avila A, Pilleggi F. A new technique to perform epicardial mapping in the electrophysiology laboratory. J Cardiovasc Electrophysiol Jun. 1996;7:531-536.

Soejima K, et al., Endocardial and epicardial radiofrequency ablation of ventricular tachycardia associated with dilated cardiomyopathy: the importance of low-voltage scars. Journal of the American College of Cardiology May 19, 2004;43:1834-1842.

Dukkipati SR et al., Long-term outcomes of combined epicardial and endocardial ablation of monomorphic ventricular tachycardia related to hypertrophic cardiomyopathy. Circ Arrhythm Electrophysiol Apr. 2011;4:185-194.

Stevenson WG, Wilber DJ, Natale A, et al. Irrigated radiofrequency catheter ablation guided by electroanatomic mapping for recurrent ventricular tachycardia after myocardial infarction: the multicenter thermocool ventricular tachycardia ablation trial. Circulation Dec. 16, 2008;118:2773-2782.

Sacher F. Tedrow UB, Field ME, Raymond JM, Koplan BA, Epstein LM, Stevenson WG. Ventricular tachycardia ablation: evolution of patients and procedures over 8 years. Circ Arrhythm Electrophysiol Aug. 2008;1:153-161.

Desjardins B, Morady F, Bogun F. Effect of epicardial fat on electroanatomical mapping and epicardial catheter ablation. Journal of the American College of Cardiology Oct. 12, 2010;56:1320-1327.

Fleming CP, Quan KJ, Rollins AM. Toward guidance of epicardial cardiac radiofrequency ablation therapy using optical coherence tomography. Journal of biomedical optics Jul.-Aug. 2010;15:041510.

Fleming CP, Eckert J, Halpern EF, Gardecki JA, Tearney GJ. Depth resolved detection of lipid using spectroscopic optical coherence tomography. Biomedical optics express 2013;4:1269-1284.

D'Avila A, Houghtaling C, Gutierrez P, Vragovic O, Ruskin JN, Josephson ME, Reddy VY. Catheter ablation of ventricular epicardial tissue: a comparison of standard and cooled-tip radiofrequency energy. Circulation May 18, 2004;109:2363-2369.

Madder RD, Khan M, Husaini M, Chi M, Dionne S, VanOosterhout S, Borgman A, Collins JS, Jacoby M. Combined Near-Infrared Spectroscopy and Intravascular Ultrasound Imaging of Pre-Existing Coronary Artery Stents: Can Near-Infrared Spectroscopy Reliably Detect Neoatherosclerosis? Circulation Cardiovascular imaging Jan. 2016;9.

Fard AM, Vacas-Jacques P, Hamidi E, Wang H, Carruth RW, Gardecki JA, Tearney GJ. Optical coherence tomography—near infrared spectroscopy system and catheter for intravascular imaging. Optics express Dec. 16, 2013;21:30849-30858.

Singh-Moon RP, Yao X, Iyer V, Marboe C, Whang W, Hendon CP. Real-time optical spectroscopic monitoring of non-irrigated lesion progression within atrial and ventricular tissues. J Biophotonics Jul. 30 2018e201800144.

Singh-Moon RP, Marboe CC, Hendon C. Near-infrared spectroscopy integrated catheter for characterization of myocardial tissues: preliminary demonstrations to radiofrequency ablation therapy for atrial fibrillation. Biomed Opt Express 2015;6:2494-2511.

Nakamori S, Nezafat M, Ngo LH, Manning WJ, Nezafat R. Left Atrial Epicardial Fat Volume Is Associated With Atrial Fibrillation: A Prospective Cardiovascular Magnetic Resonance 3D Dixon Study. Journal of the American Heart Association Mar. 23, 2018;7.

De Coster T, Claus P, Seemann G, Willems R, Sipido KR, Panfilov AV. Myocyte Remodeling Due to Fibro-Fatty Infiltrations Influences Arrhythmogenicity. Front Physiol 2018;9:1381.

De Coster T, Claus P, Kazbanov IV, Haemers P, Willems R, Sipido KR, Panfilov AV. Arrhythmogenicity of fibro-fatty infiltrations. Sci Rep Feb. 1, 2018;8:2050.

Samanta R, Pouliopoulos J, Thiagalingam A, Kovoor P. Role of adipose tissue in the pathogenesis of cardiac arrhythmias. Heart rhythm : the official journal of the Heart Rhythm Society Jan. 2016;13:311-320.

Batal O, Schoenhagen P, Shao M, Ayyad AE, Van Wagoner DR, Halliburton SS, Tchou PJ, Chung MK. Left atrial epicardial adiposity and atrial fibrillation. Circ Arrhythm Electrophysiol Jun. 2010;3:230-236.

Viles-Gonzalez JF, de Castro Miranda R, Scanavacca M, Sosa E, d'Avila A. Acute and chronic effects of epicardial radiofrequency applications delivered on epicardial coronary arteries. Circ Arrhythm Electrophysiol Aug. 2011;4:526-531.

A. N. Ganesan, N. J. Shipp, A. G. Brooks, P. Kuklik, D. H. Lau, H. S. Lim, T. Sullivan, K. C. Roberts-Thomson, and P. Sanders, "Long-term outcomes of catheter ablation of atrial fibrillation: a systematic review and meta-analysis," Journal of the American Heart Association 2, e004549 (2013).

M. A. Wood, "Exposing gaps in linear radiofrequency lesions: form before function," Circ Arrhythm Electrophysiol 4, 257-259 (2011).

C. P. Fleming, K. J. Quan, H. Wang, G. Amit, and A. M. Rollins, "In vitro characterization of cardiac radiofrequency ablation lesions using optical coherence tomography," Optics express 18, 3079-3092 (2010).

S. Iskander-Rizk, P. Kruizinga, A. F. W. van der Steen, and G. van Soest, "Spectroscopic photoacoustic imaging of radiofrequency ablation in the left atrium," Biomedical optics express 9, 1309-1322 (2018).

M. Mercader, L. Swift, S. Sood, H. Asfour, M. Kay, and N. Sarvazyan, "Use of endogenous NADH fluorescence for real-time in situ visualization of epicardial radiofrequency ablation lesions and gaps," American journal of physiology. Heart and circulatory physiology 302, H2131-2138 (2012).

R. P. Singh-Moon, X. Yao, V. Iyer, C. Marboe, W. Whang, and C. P. Hendon, "Real-time optical spectroscopic monitoring of non-irrigated lesion progression within atrial and ventricular tissues," J Biophotonics, e201800144 (2018).

J. Swartling, S. Palsson, P. Platonov, S. B. Olsson, and S. Andersson-Engels, "Changes in tissue optical properties due to radio-frequency ablation of myocardium," Medical & biological engineering & computing 41, 403-409 (2003) (Abstract only).

* cited by examiner

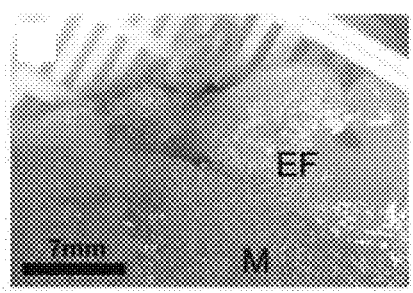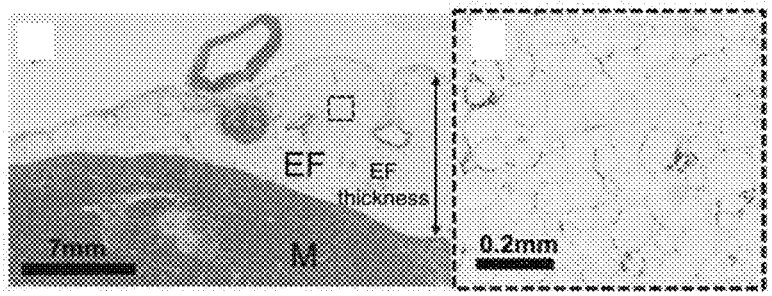
Figure 3A  Figure 3B  Figure 3C

Figure 4A
3D Scanned Model
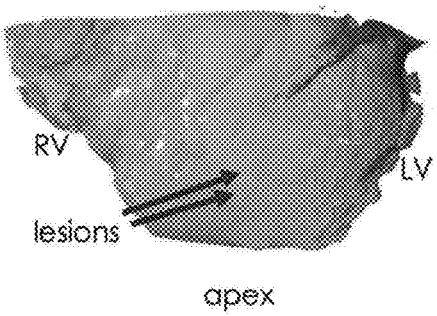
Figure 4B
Camera Tracking
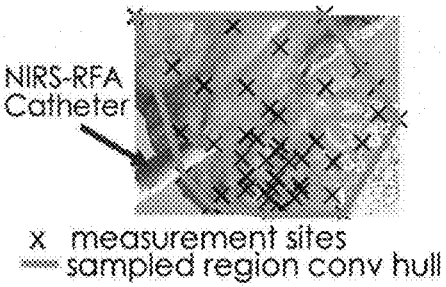
x  measurement sites
— sampled region conv hull
Adipose Distribution Map
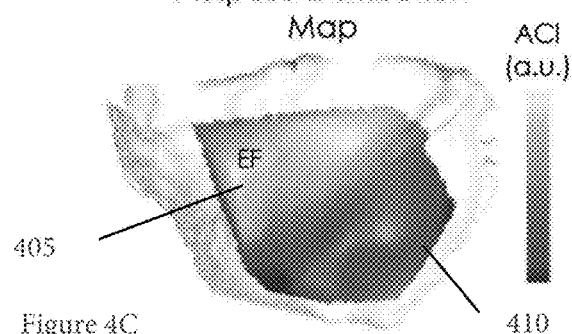
Lesion Contrast Map
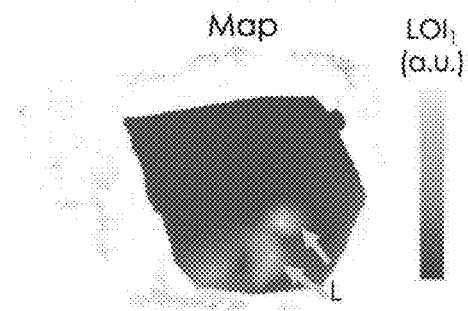
Figure 4D
Figure 4C
Composite ACI-$LOI_i$ Map
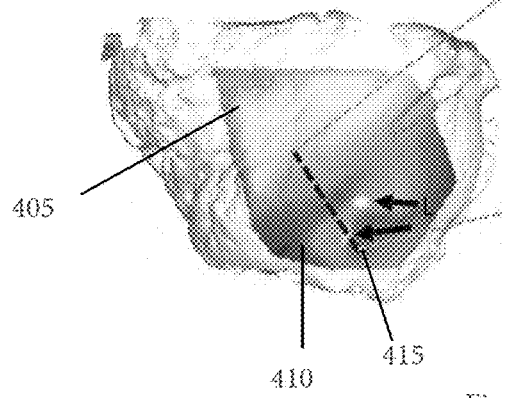
Gross pathology cross-section
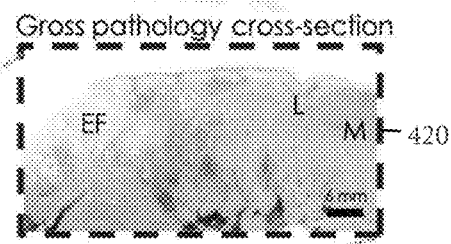
Trichome Histology
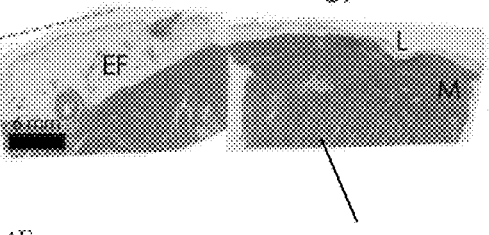
Figure 4E

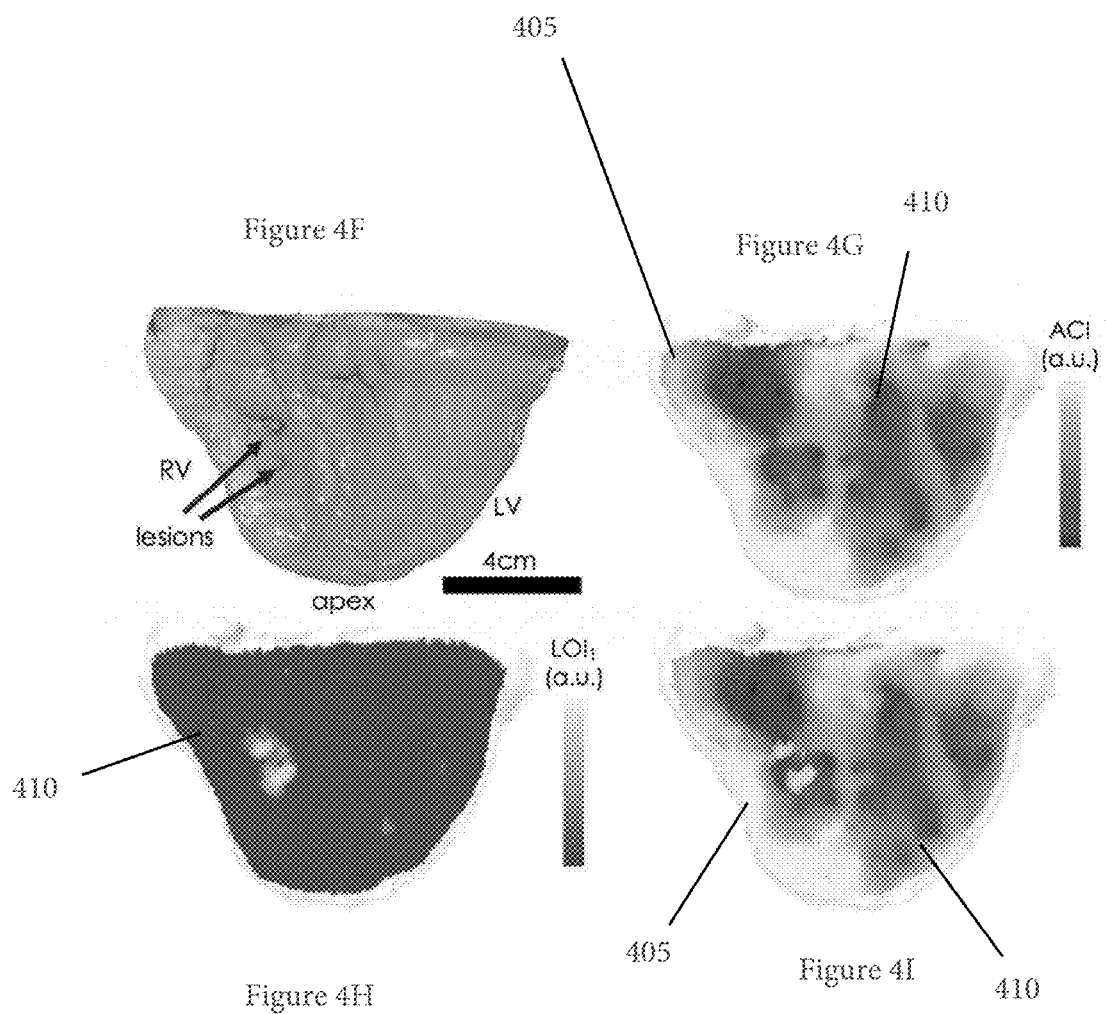

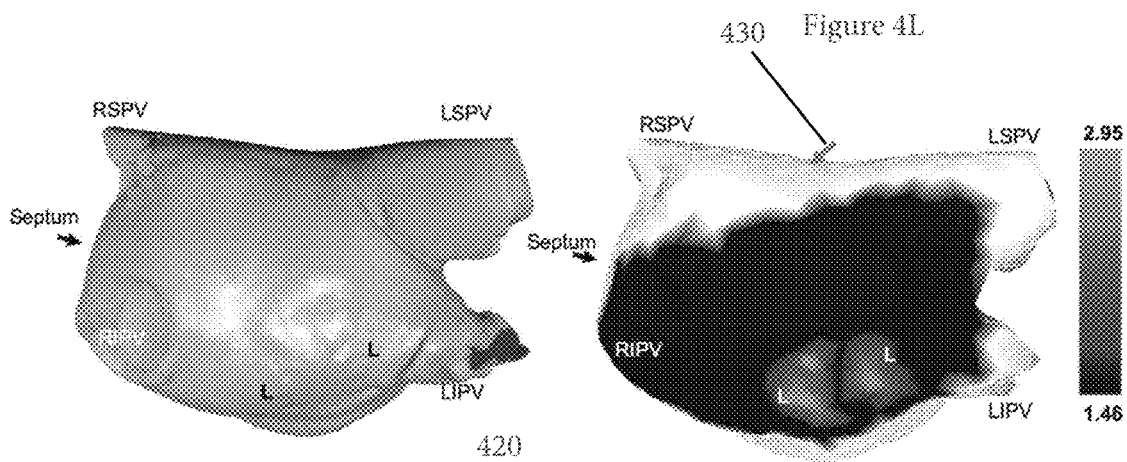
Figure 4J
Figure 4L
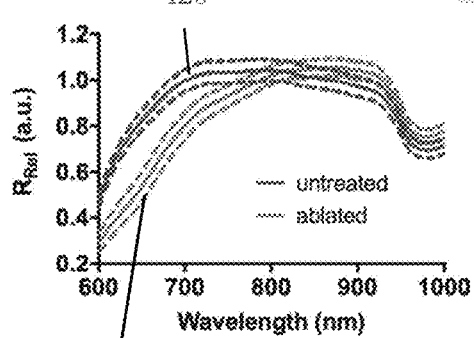
Figure 4K

SYSTEM, METHOD, COMPUTER-ACCESSIBLE AND APPARATUS FOR PROVIDING NEAR-INFRARED SPECTROSCOPY FOR ANATOMICAL MAPPING OF THE EPICARDIUM

STATEMENT REGARDING FEDERALLY SPONSORED RESEARCH

This invention was made with government support under Grant No. HL127776 awarded by the National Institutes of Health and Grant No. 1454365, awarded by the National Science Foundation. The government has certain rights in the invention.

CROSS-REFERENCE TO RELATED APPLICATION(S)

This application relates to and claims priority from U.S. Patent Application No. 62/863,483, filed on Jun. 19, 2019, the entire disclosure of which is incorporated herein by reference.

FIELD OF THE DISCLOSURE

The present disclosure relates generally to a near infrared spectroscopy, and more specifically, to exemplary embodiments of exemplary system, method, computer-accessible and apparatus for providing near-infrared spectroscopy for anatomical mapping of, e.g., the epicardium.

BACKGROUND INFORMATION

Epicardial ablation is regarded as a viable adjunct for managing a treatment of ventricular tachycardias with complex substrates. The epicardial surface is generally coated with adipose tissue and coronary vasculature, which complicates electrogram interpretation and ablation targeting, respectively. Near-infrared spectroscopy ("NIRS") is a promising tool, which has been previously used for detecting blood circulation and intravascular lipid, and thus maybe suitable for improving catheter guidance.

Epicardial ablation has grown into a viable primary and auxiliary treatment for the management of ventricular arrhythmias such as ventricular tachycardia ("Vtach"). In many cases, regions of slowed conduction, such as, for example, post-infarcted, scar border zones, can constitute the substrate for tachycardia-inducing re-entrant circuits and are therefore candidate targets for ablation. Previous reports estimate that about a third of Vtach presentations fail treatment by endocardial ablation, due in part to origins extending mid-wall or epicardially which rendering them inaccessible from the endocardium alone. While epicardial pursuit is recommended in such instances, differences between endo- and epicardial structures, such as lipid distribution and vascularity, can complicate treatment efforts. In the case of epicardial fat, its presence has been shown to limit radiofrequency ("RF") energy penetration and could also lead to ambiguities in electrograms, which can mimic scars or lesions. Moreover, due to the exposure of epicardial vessels, repeat angiograms are routinely performed during catheter navigation to avoid sequela caused by injury to coronary circulation. A procedure to facilitate tissue discernment at the catheter tip could help improve therapeutic interventions by resolving electrogram uncertainties and preventing accidental ablation of coronary vessels.

Optical coherence tomography ("OCT") has facilitated imaging of epicardial fat in histological detail. However, prior studies indicating the influence of overlying fat on ablation lesion report significant damping of RF energy penetration in fat layers (e.g., fat layers less than 3 mm), which can exceed the imaging range provided by OCT in cardiac tissue. NIRS has been widely utilized in a variety of medical applications from standard measurements of pulse oximetry to, more recently, its application toward intravascular discrimination of lipid-core plaques within coronary arteries.

Thus, it may be beneficial to provide an exemplary system, method, computer-accessible and apparatus for near-infrared spectroscopy for anatomical mapping of the epicardium, which can overcome at least some of the deficiencies, described herein above.

SUMMARY OF EXEMPLARY EMBODIMENTS

An exemplary catheter can be provided, which can include, for example a source fiber(s) configured to (i) receive a near infrared spectroscopic (NIRS) radiation, and (ii) provide the NIRS radiation to a portion(s) of a sample(s), a detection fiber(s) configured to receive a return radiation from the sample(s) that can be based on the NIRS radiation that was provided to the portion(s) of the sample(s), and an ablation electrode(s) configured to ablate the sample(s) based on the return radiation. The source fiber(s), the detection fiber(s), and the ablation electrode(s) can be integrated into the single sheath. The ablation electrode(s) can be a radiofrequency ablation electrode. The source fiber(s) and the detection fiber(s) can be spaced apart at a particular distance from one another based on a tissue absorption characteristic and a scattering characteristic of the NIRS radiation, where the particular distance can be about 0 mm to about 4 mm.

To be Added Based on Information from Investigators

In certain exemplary embodiments of the present disclosure, a broadband light source(s) can be configured to generate the NIRS radiation being received by the source fiber(s). A continuous-wave light source can be configured to generate the NIRS radiation being received by the source fiber(s). A charge coupled device can be configured to (i) receive the return radiation from the detection fiber(s), and (ii) generate imaging information based on the return radiation, where the imaging information can be associated with the portion(s) of the sample(s).

In some exemplary embodiments of the present disclosure, the source fiber(s) can include at least six source fibers, the detection fiber(s) can include at least six detection fiber, and the ablation electrode(s) can include at least twelve ablation electrodes. One of the at least six source fibers and one of the at least six detection fibers can form a pair of fibers, one of the at least twelve ablation electrodes can be disposed on a first side of the pair of fibers, another one of the at least twelve ablation electrodes can be disposed on a second side of the pair of fibers, and the first side can be disposed opposite to the second side with respect to the pair of fibers.

Additionally, an exemplary method for ablating a portion(s) of a sample(s), can be provided which can include, for example, generating a near infrared spectroscopic (NIRS) radiation, providing the NIRS radiation(s) to the portion(s) using a source fiber(s) provided in a catheter, receiving a return radiation(s) from the portion(s) that can be based on the NIRS radiation (s) that was provided to the portion(s) of the sample(s) using a detection fiber(s) provided in the catheter, and ablating the portion(s) using a radiofrequency ablation (RFA) based on the return radiation(s). The ablating the portion(s) using RFA can include ablating the portion(s) using a RFA electrode(s) integrated into the catheter. A three-dimensional position of the catheter with respect to the portion(s) can be determined. A contact between the catheter and the portion(s) can be determined.

In some exemplary embodiments of the present disclosure, the sample(s) can include a heart, and an epicardial map(s) of the heart can be generated based on the backscattered radiation(s). The epicardial map(s) can include (i) a coronary vessel(s) in the heart, (ii) fat in the heart, (iii) scar tissue on the heart, or (iv) fibrosis on the heart. A location of the coronary vessel(s) in the heart can be determined by determining a hemoglobin concentration in the heart. The hemoglobin concentration can be determined using a spectral unmixing procedure, which can be an inverse Monte Carlo procedure.

Further, an exemplary system, method, and computer-accessible medium for causing an ablation of a portion(s) of a sample(s), can include, for example, receiving information related to a backscattered radiation from the portion(s) that can be based on a near infrared spectroscopic radiation(s) provided to the sample(s), generating an epicardial map(s) of the portion(s) based on the information, determining a first location of a coronary vessel(s) using the information, and causing the ablation of the portion(s) at a second location that excludes the coronary vessel(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 3A is an exemplary image of a pathology cross-section of a heart showing epicardial fat according to an exemplary embodiment of the present disclosure;

FIG. 3B is an exemplary image of trichrome histology and measurement of epicardial fat thickness for the heart shown in FIG. 3A according to an exemplary embodiment of the present disclosure;

FIG. 3C is an exemplary microscopic image of epicardial fat according to an exemplary embodiment of the present disclosure;

FIG. 4A is an exemplary three-dimensional scanned model obtained from scanning of the ventricles according to an exemplary embodiment of the present disclosure;

FIG. 4B is an exemplary image of the sampled region of optical measurements of a heart tracked by a camera according to an exemplary embodiment of the present disclosure;

FIG. 4C is an exemplary adipose distribution map of the heart according to an exemplary embodiment of the present disclosure;

FIG. 4D is an exemplary lesion contrast map according to an exemplary embodiment of the present disclosure;

FIG. 4E is an exemplary composite overlay of adipose and thresholded lesion contrast maps according to an exemplary embodiment of the present disclosure;

FIGS. 4F-4I are exemplary high-density maps of epicardial surface with 202 measurements according to an exemplary embodiment of the present disclosure;

FIG. 4J is an exemplary image of a textured 3-D scanned mesh of an inverted human left atrial sample according to an exemplary embodiment of the present disclosure;

FIG. 4K is an graph indicating mean (+/−95% CI) spectra taken from all untreated and ablated regions within the sample according to an exemplary embodiment of the present disclosure;

FIG. 4L is an exemplary LOI map derived from NIRS measurements and rendered onto the 3-D scanned geometry according to an exemplary embodiment of the present disclosure;

Figure 1A:
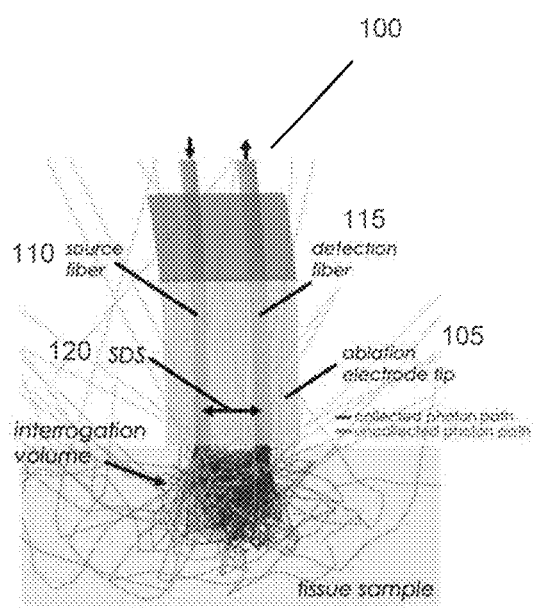
FIG. 1A is an exemplary diagram of an exemplary near-infrared spectroscopy integrated catheter according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

An exemplary apparatus, which included optical fibers integrated into a commercial radiofrequency ablation ("RFA") catheter that facilitated near infrared ("NIR") or NIRS measurement at the tip electrode. A series of unstructured measurements were made over the epicardial surface of resected ventricles obtained from human donor hearts (e.g., n=9). The NIRS catheter optical configuration was designed to bias measurement sensitivity toward tissue absorption to emphasize attenuation by molecular constituents. A new exemplary parameter was developed, the adipose contrast index ("ACI"), based on spectral morphological features corresponding to lipid absorption. Using point cloud measurement co-registration and a triangulation-based interpolation procedures, three-dimensional ("3D") renderings of epicardial adipose distributions were obtained. NIRS-derived ACI maps were subject to comparison with gross pathology and histological analysis to examine the degree of correspondence with the spatial deposition of lipid. Histological validation across measured and interpolated sites showed strong correlation (e.g., Pearson's, R=0.903) between ACI values and local fat layer thickness. The exemplary apparatus can be used for coronary vessel detection and confirmation of acute epicardial lesion delivery. The exemplary system, method, and computer-accessible medium, according to an exemplary embodiment of the present disclosure can identify coronary vessels that should be avoided, fat that can alter energy delivery, and/or scar or fibrosis which can be a target for ablation therapy.

The exemplary system, method computer-accessible medium, and apparatus, according to an exemplary embodiment of the present disclosure, can include a custom NIRS-integrated ablation catheter. The optical configuration can bias measurements influence toward attenuation by molecular absorbers. ACI, which can be used to estimate the local tissue lipid content from NIRS measurements. Three-dimensional renderings of NIRS-extracted ACI can be correlated with histological fat thickness assessment. The extension of NIRS toward coronary vessel detection and additionally mapping of lesion delivery has been provided using a previously reported lesion contrast parameter, the lesion optical index.

Exemplary Methods

Human donor hearts (e.g., n=9) were acquired Table 1 below shows a summary of donor medical histories for the hearts used in this study. Experiments were conducted within 24-48 hrs following donor expiration. Ventricular halves were surgically resected and submerged under temperature-maintained (e.g., 37° C.) phosphate buffered saline using a circulating water bath system. A commercial irrigated RFA catheter (e.g., Thermocool, Biosense Webster, USA), generator (e.g., Stockert 70, Biosense Webster, USA) and irrigation system (e.g., CoolFlow, Biosense Webster, USA) was utilized to delivery lesion sets over the epicardial surface. To create lesions of different sizes, ablation duration was varied between about 10-60 s, while power and flow rate settings were fixed at about 30 W and 5 mL/min, respectively. Following lesion delivery, hearts were 3D scanned to obtain a point cloud of the ventricular surface. After scanning, the specimen was situated on a platform for subsequent epicardial NIRS sampling with camera tracking of sampled sites. An average of 68 measurements across the epicardial surface were obtained to evaluate the impact of increased spatial sampling.

TABLE 1

Donor Medical Histories (n = 9).

| Heart # | Age | Sex | Disease History | Cause of Death |
|---|---|---|---|---|
| 1 | 70 | M | AF, CAD, HTN, MI | CA |
| 2 | 38 | M | CAD, HTN, DVT | STEMI |
| 3 | 57 | F | TB, S | CA |
| 4 | 57 | M | COPD, DVT | RF |
| 5 | 66 | M | CAD, HTN, DVT | STEMI |
| 6 | 57 | F | CAD, COPD, HTN | S |
| 7 | 69 | M | DM, CHF, HTN, CKD | ICH |
| 8 | 46 | M | KF | CPA |
| 9 | 54 | M | CAD, HTN | STEMI |

AF—atrial fibrillation; CAD—coronary artery disease; HTN—hypertension; MI—myocardial infarction; DVT—deep vein thrombosis; TB—tuberculosis; S—stroke; RF—respiratory failure; STEMI—ST elevation MI; COPD—chronic obstructive pulmonary disorder; DM—diabetes type 2; CHF—congestive heart failure; CKF—chronic kidney disease; KF—kidney failure; ICH—intracerebral hemorrhage; CPA—cardiopulmonary arrest.

For vessel detection experiments, the left anterior descending ("LAD") artery was identified and cannulated. Whole swine blood acquired from the butcher was perfused through the vessel with pulsatile flow. Flow settings were adjusted between 0-15 mL/min to mimic different heart rates. NIRS measurements were made on the vessel surface during perfusion to assess the feasibility of vessel detection.

Exemplary Optical Catheter Design

FIG. 1A shows an exemplary diagram of the exemplary NIRS-integrated RFA catheter 100 according to an exemplary embodiment of the present disclosure, where the fibers and the ablation electrode are integrated into a single sheath. A custom tip electrode 105 can be fabricated to accommodate NIRS illumination and sampling of tissue backscattered light. A collection of optical fibers (e.g., source fiber 110 and detection fiber 115) can be integrated with, e.g., a commercial RFA catheter. The fiber between the illumination and collection fibers can be adjusted to bias measurement influence toward tissue absorption and minimize the influence of scattering. The source-detector separation ("SDS") 120 can be a design parameter, which can affect the amount of collected light and its sensitivity to absorbing molecules. The SDS can vary from about 0 mm plus or minus about 10% (e.g., if a single fiber is used as discussed below) to about 4 mm plus or minus about 10%. Examples of measurements obtained with a catheter having a 2.3 mm SDS are shown as lines 125 and 130 in FIG. 1B, which illustrate the normalized reflectance spectra for cardiac muscle and epicardial fat. A broadband lamp (e.g., HL-2000HP, Ocean Optics Inc., Dunedin, FL) can be used for tissue illumination and the diffusely backscattered collected light from the tissue was recorded by a spectrometer (e.g., 600-1000 nm) (e.g., C9405CB, Hamamatsu, Bridgewater, NJ).

As shown in FIG. 1A, source fiber 110 and detection fiber 115 are illustrated as to fibers. However, a single fiber can be used, which can operate as both source fiber and detection fiber.

Exemplary NIRS Model-Based Processing

Figure 1B:
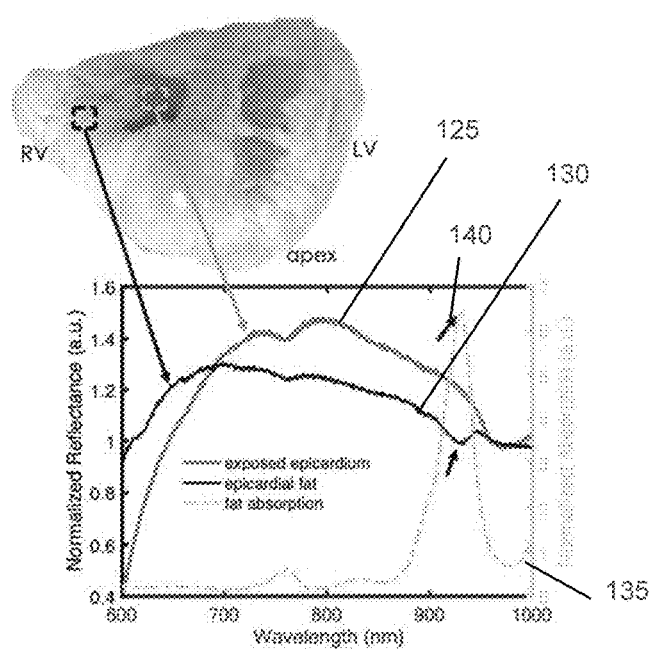
FIG. 1B is an exemplary image of a heart and a corresponding graph of near-infrared reflectance spectra according to an exemplary embodiment of the present disclosure.

NIR spectral measurements were calibrated into relative reflectance ("$R_{Rel}$"). This included dark subtraction, system-response correction, and normalization from a measurement taken on a phantom of known optical properties. FIG. 1B illustrates the exemplary absorption spectrum of fat along with NIRS measurement for a lipid rich and lipid scarce area according to an exemplary embodiment of the present disclosure. The local minima in the $R_{Rel}$ spectra centered at 930 nm reflects a relative decrease in collected light due to strong attenuation of the signal by lipid. The reflectance spectra normalized at 960 nm for sites absent of, and richly coated with, epicardial fat (e.g., exposed epicardium indication by line 125 and epicardial fat indicated by line 130) for a given sample. The absorption spectrum of lipid (e.g., indicated by fat absorption line 135) is also shown in FIG. 1B. Arrows 140 indicate local minima centered at 930 nm reflectance corresponding to a strong lipid absorption peak. Based on changes in spectral morphology, a new parameter has been provided, the ACI, developed to accentuate lipid regions. Two exemplary equations can be used (e.g., Eq. (1) and Eq. (3)). Thus, for example:

$$ACI = \sqrt{\int_\Lambda \frac{R_{Rel}(\lambda)}{R_{Rel}(960 \text{ nm})} d\lambda} \quad (1)$$

where $\Lambda$ can be the spectral region 600-1000 nm. In order to map ablated sites, the lesion optical index ("$LOI_1$") was also computed, for example, as follows:

$$LOI_1 = \frac{R_{Rel}(960 \text{ nm})}{R_{Rel}(616 \text{ nm})} \quad (2)$$

$$ACI = 1 + \int_{\Lambda_b}^{\Lambda_e} R'_{Rel}(\lambda) - R'_{Rel}(910 \text{ nm}) = \quad (3)$$

$$1 + [R_{Rel}]_{\Lambda_b}^{\Lambda_e} - R'_{Rel}(910 \text{ nm}) \cdot [\lambda]_{\Lambda_b}^{\Lambda_e}$$

where $\Lambda_b$ and $\Lambda_e$ denote the beginning and the ending wavelengths used for integration. In order to map ablated sites, the lesion optical index ($LOI_1$) was also computed using Eq. (2).

For hemoglobin tracking, measurements were fit to a model-based, spectral unmixing procedure known as the inverse Monte Carlo ("MC") method. This exemplary procedure utilizes simulations of probe light transport to determine the chemical concentrations of molecular absorbers for a given NIRS reflectance spectrum. This model was used to extract total hemoglobin time courses during coronary vessel perfusion.

Exemplary Point-Cloud Co-Registration

Figure 2:
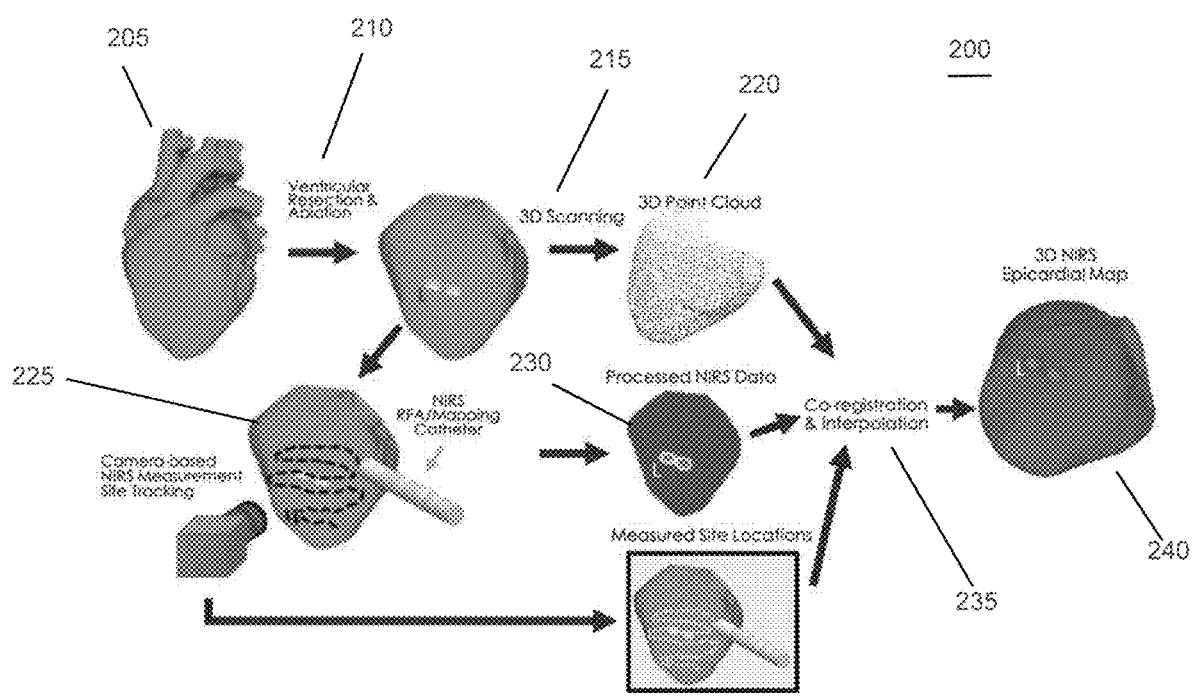
FIG. 2 is an exemplary flow diagram of near-infrared spectroscopic ventricular mapping according to an exemplary embodiment of the present disclosure.

Following RFA, and prior to optical NIRS mapping, ventricular halves were 3D scanned to generate a point cloud (e.g., a set of data points with corresponding 3D coordinates) of the epicardial surface topology. (See, e.g., FIG. 2). In particular, FIG. 2 shows an exemplary flow illustration of a method 200 for near-infrared spectroscopic ventricular mapping according to an exemplary embodiment of the present disclosure. After heart 205 was ablated at procedure 210 (e.g., ventricular resection and ablation), a scan was performed at procedure 215. As shown in FIG. 2, optical measurements were taken across the epicardial surface with simultaneous camera tracking of sampled locations at procedure 225. A set of affine transformations were applied to optimally orient the three-dimensional (3D) point cloud 220 such that the two-dimensional ("2D") projection matched the camera image. This facilitated a linear transfer relationship between camera image pixel coordinates and the 2D projection of the point cloud. NIRS-derived parameters 230 for each measured site was then interpolated (e.g., bi-harmonic) at procedure 235 over a structured grid enclosed by the convex hull of the measurement sites and mapped onto the 3D surface to generated 3D NIRS epicardial map 240. This exemplary method can function as a surrogate for clinical mapping systems, which can be used to track the position of the electrical measurement, and can create a shell using measured and interpolated values.

Exemplary Histopathology

Following NIRS sampling, hearts were fixed in formalin, and then cut obliquely across the optically sampled region. These slices were photographed for macroscopic assessment and paraffin-embedded for subsequent histological processing. Five micrometer thick serial sections were cut and stained with hematoxylin and eosin (H&E) and Masson's trichrome Stained sample slides were digitized under 20× magnification and analyzed. Slide images were reviewed by a board-certified pathologist and local epicardial fat thickness was measured for correlational purposes. (See e.g., FIGS. 3A-3C). In particular, FIG. 3A shows an exemplary image of a pathology cross-section of a heart showing epicardial fat, FIG. 3B illustrates an exemplary image of trichrome histology and measurement of epicardial fat thickness for the heart shown in FIG. 3A, and FIG. 3C shows an exemplary microscopic image of epicardial fat according to an exemplary embodiment of the present disclosure.

Exemplary Statistical Analysis

Correspondence between ACI values extracted over measured and interpolated sites and histologically-derived fat layer thickness was quantified using the Pearson's correlation coefficient. Significance was marked by p-values less than 0.05. Prism 8 software (e.g., Graphpad, San Diego, CA) was used for all statistical analyses.

Exemplary Results

FIGS. 4A-4E show exemplary three-dimensional renderings of ACI and $LOI_1$ maps. In particular, FIG. 4A illustrates an exemplary 3D scanned model (e.g., 3D mesh) obtained from 3D scanning of the ventricles according to an exemplary embodiment of the present disclosure. FIG. 4B shows an exemplary image of the sampled region of optical measurements of a heart tracked by a camera according to an exemplary embodiment of the present disclosure. FIG. 4C illustrates an exemplary diagram illustrating the spatial distribution of the ACI rendered onto the 3D scanned point cloud topology according to an exemplary embodiment of the present disclosure. FIG. 4D shows an exemplary spatial distribution of the lesion contrast parameter, the LOI1 according to an exemplary embodiment of the present disclosure. FIG. 4E illustrates an exemplary composite overlay of adipose and thresholded lesion contrast maps according to an exemplary embodiment of the present disclosure. A cross-section 415 of the tissue was taken along a region demonstrating a lesion and transition from a thick to thin epicardial fat coating. NIRS maps showed good agreement with gross pathology (e.g., area 420) and histological correlates (e.g., area 425) of treatment and fat thickness.

FIGS. 4F-4I show exemplary high-density maps of epicardial surface with 202 measurements according to an exemplary embodiment of the present disclosure. In particular, FIG. 4F illustrates an exemplary 3D mesh obtained from 3D scanning of the ventricles. FIG. 4G shows the exemplary spatial distribution of the ACI rendered onto the 3D scanned point cloud topology. Greater detail in fat distribution can be seen with the increased sampling. FIG. 4H illustrates the exemplary spatial distribution of the LOI1. FIG. 4I shows a composite overlay of both adipose and the thresholded lesion contrast maps.

Regions rich in epicardial fat had an orange-yellow appearance on photograph gross pathology and 3D scanned mesh renderings (e.g., indicated by regions 405 in FIGS. 4A-4I, as applicable). The spatial deposition of fat was well-represented in ACI maps. Regions without epicardial fat were well-defined in contradistinction to ACI maps (e.g., ACI values<0.4). ACI values over visibly exposed muscle demonstrated low-to-moderate values (e.g., about 0.1-0.4) which may be due to both a thin fat layer or diffusely integrated lipid infiltration within the myocardial wall. For lesion tracking, maps with LOI1 values less than about 1.5 demonstrated the detection of RFA treatment sites as confirmed by trichrome histology (e.g., regions 410). While the location of the lesion sets was identified within spatial maps of the LOI1 parameter, individual lesions were difficult to discriminate. This can be indicative of a minimum spatial sampling requirement. Qualitatively, finer details within both LOI1 and ACI distributions were better appreciated within maps rendered from the more densely sampled heart. (See e.g., FIGS. 4F-4I).

FIG. 4J shows an exemplary image of a textured 3-D scanned mesh of an inverted human left atrial sample according to an exemplary embodiment of the present disclosure. FIG. 4K illustrates an exemplary graph indicating mean (+/−95% CI) spectra (e.g., untreated 420 and treated 425) taken from all untreated and ablated regions within the sample according to an exemplary embodiment of the present disclosure. FIG. 4L shows an exemplary LOI map derived from NIRS measurements and rendered onto the 3-D scanned geometry according to an exemplary embodiment of the present disclosure. Arrow 430 in FIG. 4L indicates unevaluated mesh outside of the sampled region. The bar is 3 cm.

Exemplary Comparison Between ACI Vs Fat Layer Thickness

Figure 5:
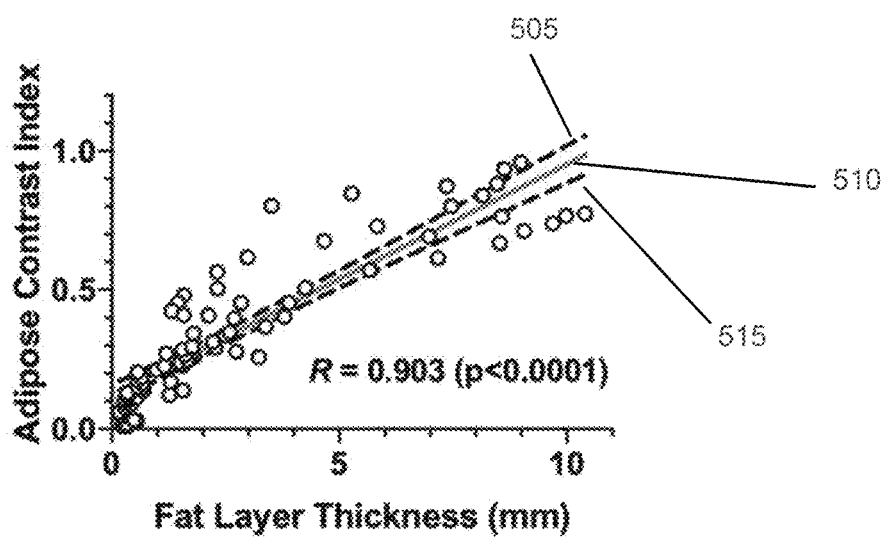
FIG. 5 is an exemplary graph illustrating the relationship between adipose contrast index and histologically-measured epicardial fat thickness according to an exemplary embodiment of the present disclosure.

ACI data from derived map were sampled along linear segments between identifiable landmarks for all hearts similar to that which is shown in FIG. 4E. These values were compared to the corresponding histologically-determined fat layer thickness. A subset of five hearts were used with 31 points sampled from each heart (e.g., a total of n=155 comparison points). Fat tissue identified by the regions of honeycomb-like appearance within histological images. (See e.g., FIG. 2C). Comparisons for extracted epicardial fat layer thicknesses and ACI values along the over the same regions are illustrated in FIG. 5. In particular, FIG. 5 shows an exemplary graph illustrating the relationship between adipose contrast index and histologically-measured epicardial fat thickness according to an exemplary embodiment of the present disclosure. ACI values were commensurate with fat layer thickness over the range of values studied (e.g., Pearson's, R=0.884, p<0.0001). Line segments across ACI maps were sampled according to corresponding tissue dissected and preserved regions. Histological evaluation of fat thickness correlated linearly to ACI values (e.g., Pearson's, R=0.884, p<0.0001, n=155, 5 hearts, 31 points per heart) up to 10 mm. Line 510 represents the mean, and lines 505 and 515 represent 95% confidence interval.

Exemplary Coronary Vessel Detection

Figure 6A:
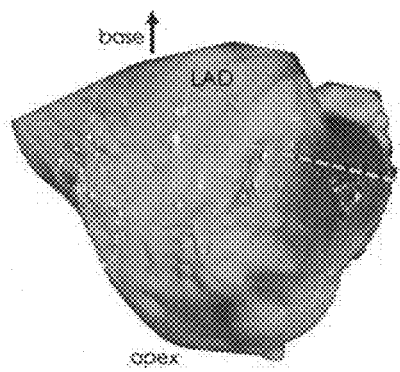
FIG. 6A is an exemplary three-dimensional scanned model of a heart according to an exemplary embodiment of the present disclosure.
Figure 6B:
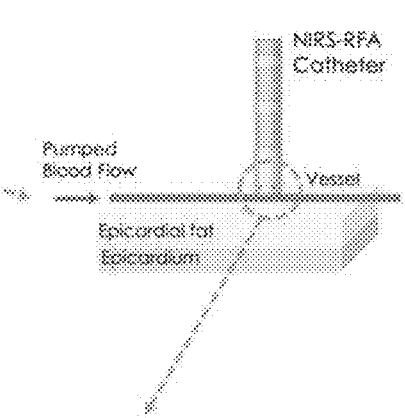
FIG. 6B is an exemplary diagram of a near-infrared spectroscopic radiofrequency ablation catheter shown analyzing epicardial fat according to an exemplary embodiment of the present disclosure.
Figure 6C:
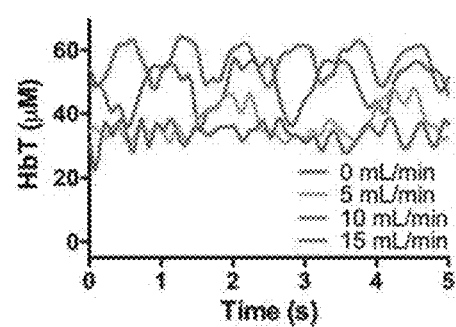
FIG. 6C is an exemplary graph illustrating derived total hemoglobin concentrations using a previous spectral unmixing procedure according to an exemplary embodiment of the present disclosure.

NIRS measurements were taken in contact with the cannulated LAD artery during pulsatile blood perfusion. (See, e.g., FIGS. 6A and 6B). Following spectral decomposition using the inverse MC processing method, oscillatory dynamics within total hemoglobin concentrations were detected and corresponded well to pump flow rate settings. (See e.g., FIG. 6C). FIG. 6A shows an exemplary 3D scanned model of the LAD artery according to an exemplary embodiment of the present disclosure. FIG. 6B illustrates an exemplary diagram of a NIRS RFA shown analyzing epicardial fat according to an exemplary embodiment of the present disclosure. The exemplary experiment shown in FIG. 6B included LAD cannulation and perfusion with whole blood under simultaneous optical measurement. FIG. 6C shows an exemplary graph illustrating derived total hemoglobin concentrations using a previous spectral unmixing procedure, the inverse Monte Carlo method. Vessel-catheter contact was confirmed by detection of pulsatile HbT dynamics, which corresponded with flow rate settings.

Exemplary Discussion

An exemplary NIRS-integrated catheter and an exemplary mapping procedure can be provided to track the distribution of epicardial features including adipose, acute lesions, and detect coronary vessels. Electroanatomical mapping of the epicardial substrate can be performed to identify ablation targets and evaluate success lesion delivery. Visceral fat layers of sufficient thickness can exhibit a drop in electrical voltage, which can also be misconstrued as post-infarct scar or necrotic lesions, each of which can utilize different responses. Fat interposition has been shown to limit radiofrequency energy penetration and thus lesion delivery. Prior studies showed that layers of fat (e.g., less than mm in thickness) utilized greater power and irrigation settings to produce comparable lesion sizes compared to thinner fat layer impositions. The capability for differentiating tissue types through with ACI and $LOI_1$ maps can facilitate the resolving of ambiguities in electrogram measurement and better inform ablation strategies. Additionally, prior studies have posited that presence of epicardial fat can play a significant role in the pathogenesis of arrhythmias. The exemplary system, method, computer-accessible medium, and apparatus can be used to assess the role of fat and its spatial distribution on the arrhythmias.

Previously, quantification of fat volume over the heart surface has been demonstrated using magnetic resonance ("MR") and computed tomography ("CT")-based imaging procedures. While accurate assessment can be performed, these procedures can add additional time and cost to the procedure and may be contraindicated in patients with implantable devices such as pacemakers. ACI values presented in the exemplary embodiments of the present disclosure were calculated in <0.23 ms on average making it suitable for real-time, ad-hoc assessment of lipid and lesion extent. Furthermore, distributions can be acquired alongside the initial electrical mapping phase adding little to no additional time to the procedure. Moreover, radiofrequency ablation treatment near coronary vessels can risk vessel trauma, which can lead to downstream sequela. NIRS-detection of vasculature through assessing dynamics in total hemoglobin concentrations can reduce the need for repeated angiograms when positioning catheters to avoid vessel injury.

Figure 7A:
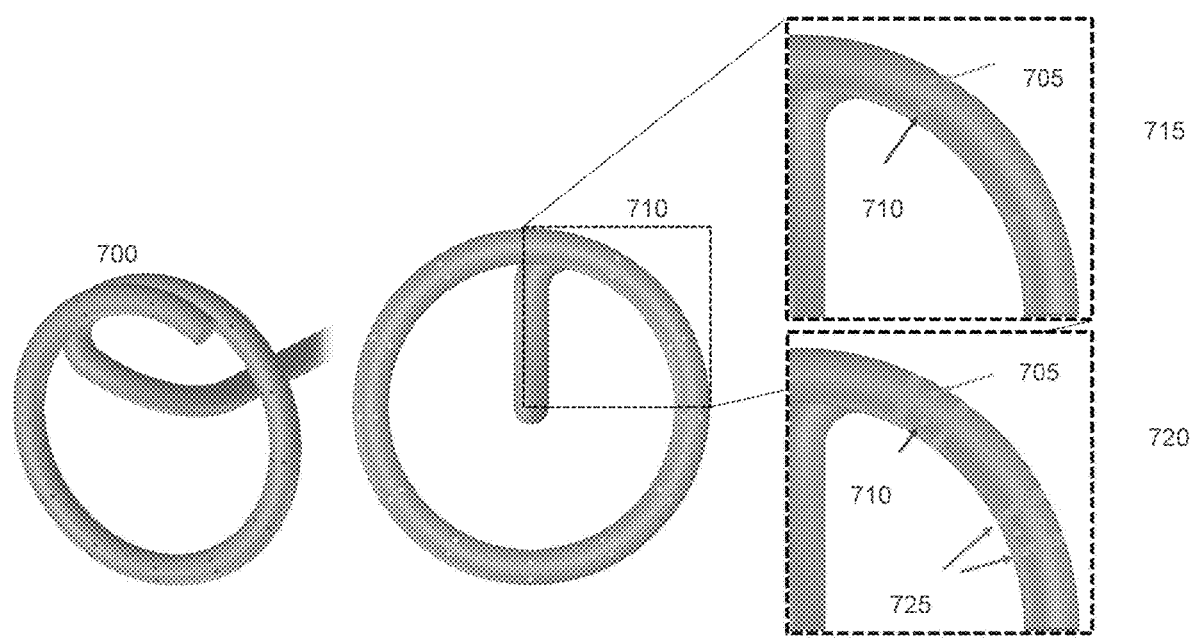
FIG. 7A is a set of exemplary diagrams of a near-infrared spectroscopic LASSO mapping catheter according to an exemplary embodiment of the present disclosure.
Figure 7B:
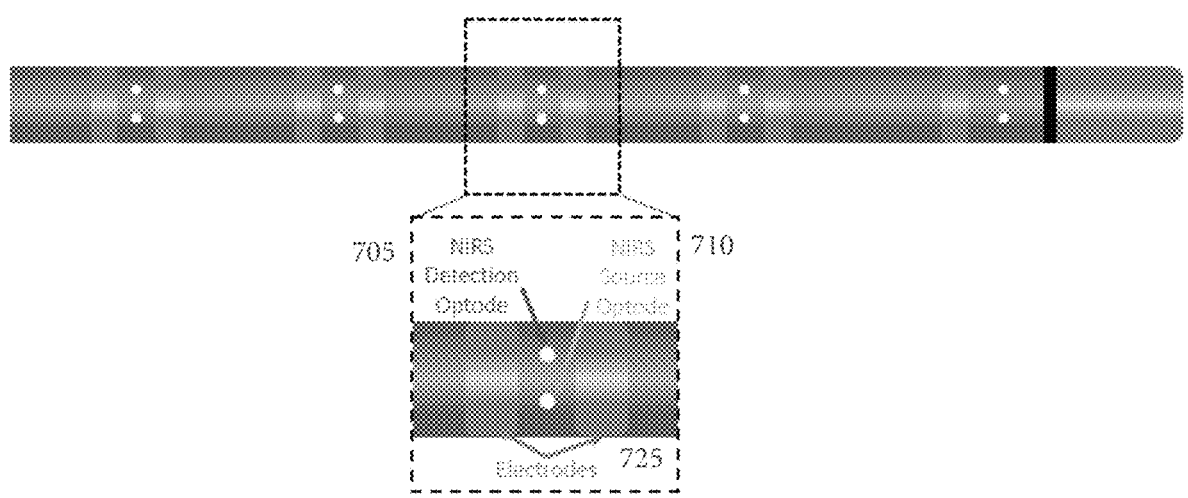
FIG. 7B is a further exemplary diagram of a near-infrared spectroscopic LASSO mapping according to an exemplary embodiment of the present disclosure.

FIGS. 7A and 7B show a set of exemplary diagrams of a near-infrared spectroscopic LASSO mapping catheter according to an exemplary embodiment of the present disclosure. For example, multiple pairs of NIRS source optode 705 and NIRS detection optodes 710 can be placed around the catheter 700, which can change the inner diameter. This can be, for example, as a NIRS mapping catheter 715 alone, or a NIRS-Integrated electroanatomical mapping catheter 720, that can have NIRS source optodes 705, NIRS detection optodes 710, and electrodes 725. The distance between optodes 705 and 710 can determine the sampling volume. The number of pairs can range from 6 to 12 pairs.

Figure 8:
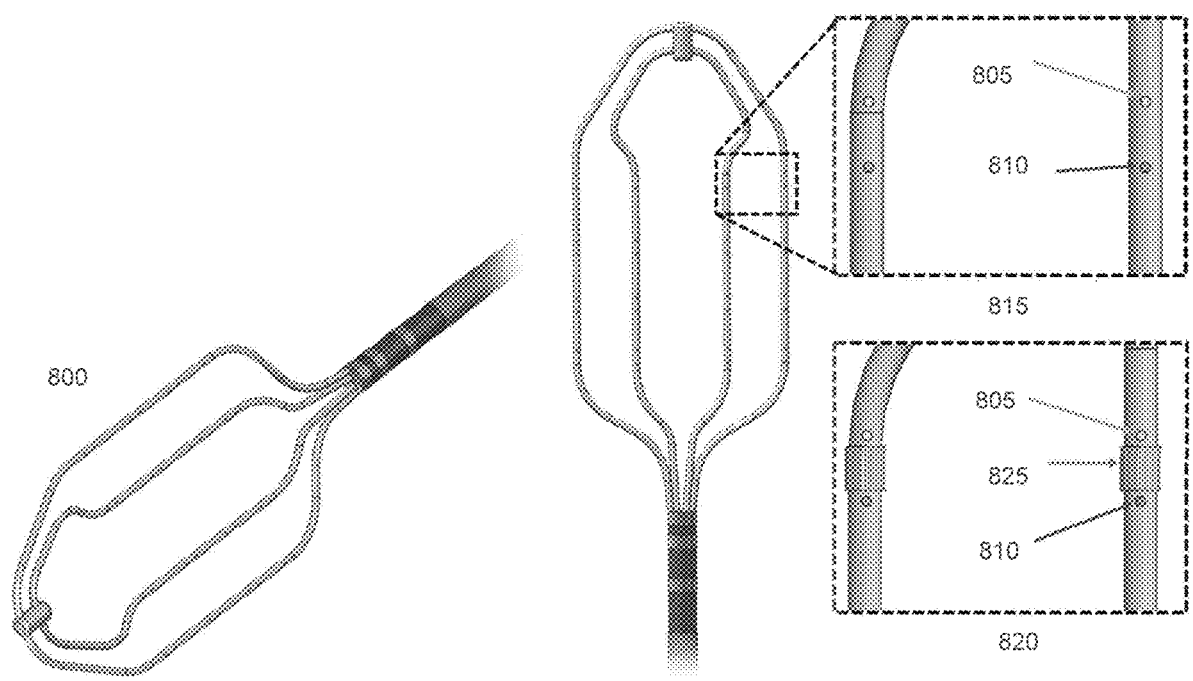
FIG. 8 is a set of diagrams of a near-infrared spectroscopic high-density grid mapping catheter according to an exemplary embodiment of the present disclosure.

FIG. 8 shows a set of diagrams of a near-infrared spectroscopic high-density ("HD") grid mapping catheter according to an exemplary embodiment of the present disclosure. An example of NIRS source 805 and detection optodes 810 are shown within a high density Grid mapping configuration. This can be shown as an NIRS grid mapping catheter 815 or NIRS 820 integrated grid electro anatomical mapping catheter. NIRS 840 can include electrodes 850 in addition to NIRS 805 source and detector pairs 810 surrounding each electrode 825.

Figure 9:
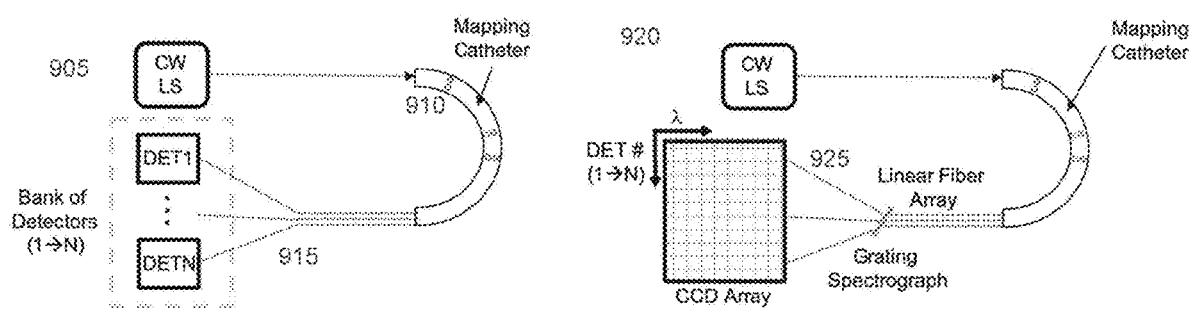
FIG. 9 is a set of diagrams of parallel acquisition procedures with continuous-wave illumination according to an exemplary embodiment of the present disclosure.

FIG. 9 shows a set of diagrams of parallel acquisition procedures with continuous-wave illumination according to an exemplary embodiment of the present disclosure. In diagram 905, tissue reflected light can be acquired from N detection sites 910 simultaneously using a set of dedicated spectrometers 915; one for each detection optode. Diagram 920 demonstrates an exemplary alternative to configuration, which can use a 2D custom spectrometer 925, which can images wavelength-discriminated detected signals onto a Charged Coupled Device ("CCD") array. A continuous-wave light source can be used for illumination in both cases, and can be distributed across each source optode simultaneously.

Figure 10:
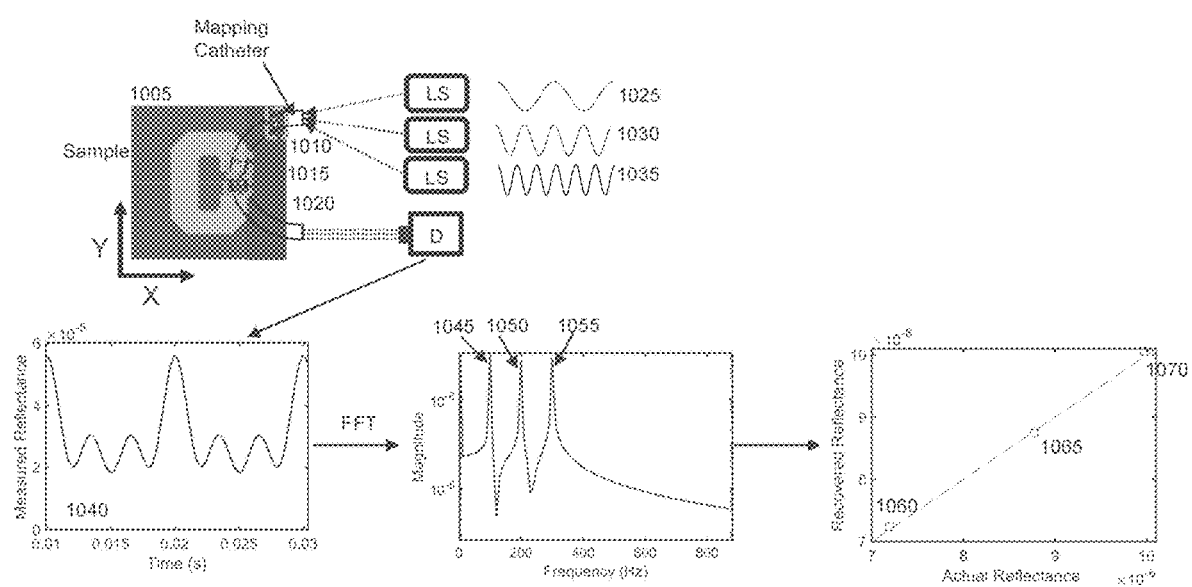
FIG. 10 is an exemplary simulation and corresponding exemplary graphs of multi-site recording of reflectance spectra using a temporally modulated procedure to encode optode according to an exemplary embodiment of the present disclosure.

FIG. 10 shows an exemplary simulation and corresponding graphs of multi-site recording of reflectance spectra using a temporally modulated procedure to encode optode according to an exemplary embodiment of the present disclosure. For example, FIG. 10 shows a measurement on a heterogeneous sample (e.g., line 1005) with 3 detection sites on the mapping catheter 1010, 1015, and 1020. The illumination channel from fiber pairs 1010, 1015, and 1020 can be intensity modulated at unique frequencies 1025, 1030, and 1035, respectively. A common detector can collect the aggregate signal from multiple detection sites 1040. The frequency content of the detected signal can be decomposed using a Fourier transform and the magnitude of the corresponding input frequencies can be taken as the recovered signal. Magnitude peaks 1045, 1050, and 1055 can correspond to measurements taken at sites 1010, 1015, and 1020, respectively. Agreement between reflectance measurement 1060, 1065, and 1070 and the standard steady state illumination scheme is shown for the 3 channels (e.g., channels 1010, 1015, and 1020).

Figure 11:
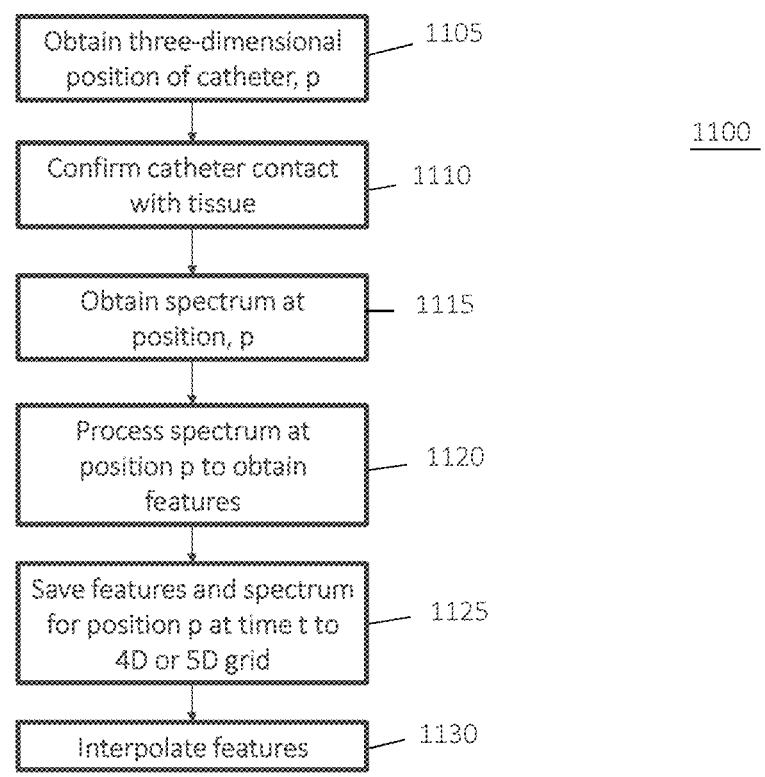
FIG. 11 is an exemplary flow diagram of a method for a full imaging pipeline according to an exemplary embodiment of the present disclosure.

FIG. 11 shows an exemplary flow diagram of a method 1100 for a full imaging pipeline according to an exemplary embodiment of the present disclosure. The exemplary flow diagram includes positioning of the catheter, and follows the data path from the moment a measurement is taken to the corresponding update of the interpolate feature map. The process is repeated at a constant sampling rate for each measurement. In particular, at procedure 1105, the 3D position of the catheter can be obtained. At procedure 1110, catheter contact with the tissue can be confirmed. At procedure 1115, the spectrum at the catheter position can be obtained. At procedure 1120, the spectrum at the position can be processed to obtain one or more features. At procedure 1125, the features and the spectrum for the position at a particular time can be saved. At procedure 1130, the features can be interpolated.

Figure 12:
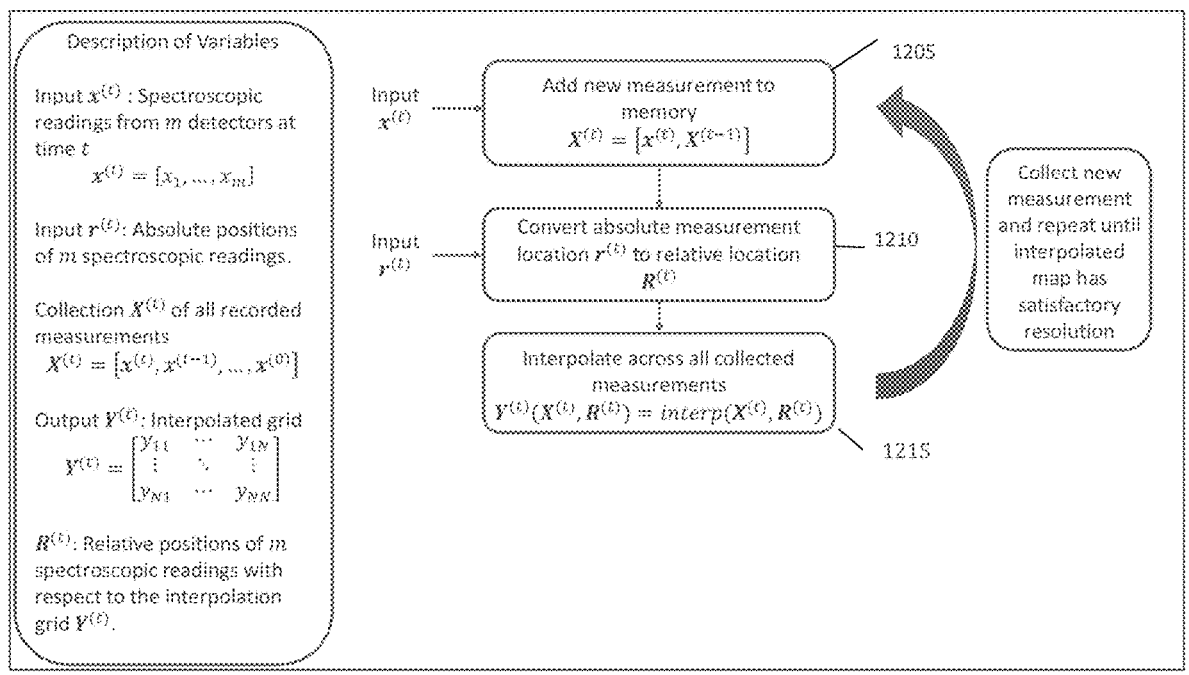
FIG. 12 is an exemplary flow diagram of a processing pipeline according to an exemplary embodiment of the present disclosure.
Figure 13:
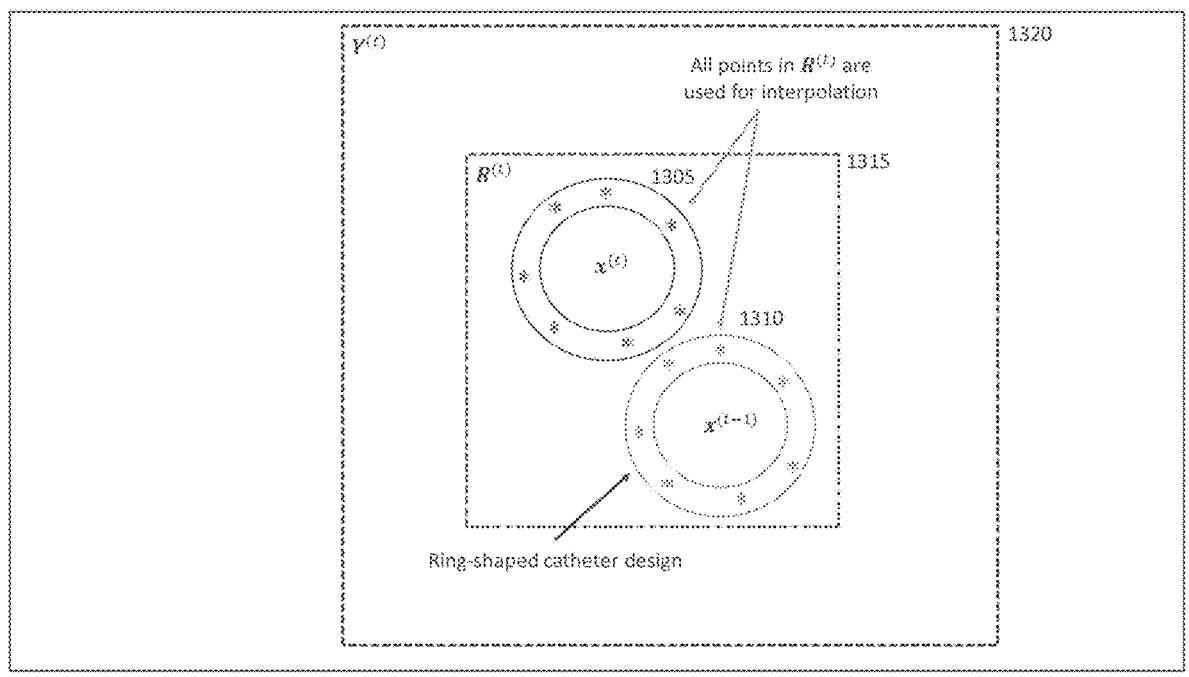
FIG. 13 is an exemplary diagram of the layout of real-time mapping using a LASSO catheter according to an exemplary embodiment of the present disclosure.

FIG. 12 shows an exemplary diagram of a processing pipeline according to an exemplary embodiment of the present disclosure. Spectroscopic measurements and their corresponding locations are provided by the catheter and imaging hardware. The input can be supplied to the host computer and stored continuously at a constant sampling rate based on hardware specifications at procedure 1205. As new data comes in, measurement locations can be mapped to their locations relative to previous measurements at procedure 1210, and the map can be updated by re-interpolating all the collected data at procedure 1215. The exemplary process can cyclically continue until the particular density of measurements within the region of interest has been collected. Feedback of the quality of the map can be assessed and displayed to the user in real-time, along with the map itself FIG. 13 shows an exemplary diagram of the layout of real-time mapping using the exemplary LASSO catheter according to an exemplary embodiment of the present disclosure. For example, FIG. 13 illustrates a layout of the exemplary real-time mapping using the exemplary LASSO catheter 1305 and 1310. Sample points collected at time t (e.g., shown by element 1305) are interpolated with neighboring samples from previous measurements (e.g., shown by element 1315). The samples chosen from previous methods can be those that fall within an ROI (R) (e.g., shown by element 1310) based on the current catheter position with respect to the total area to be mapped (Y) (e.g., shown by element 1320).

Figure 14:
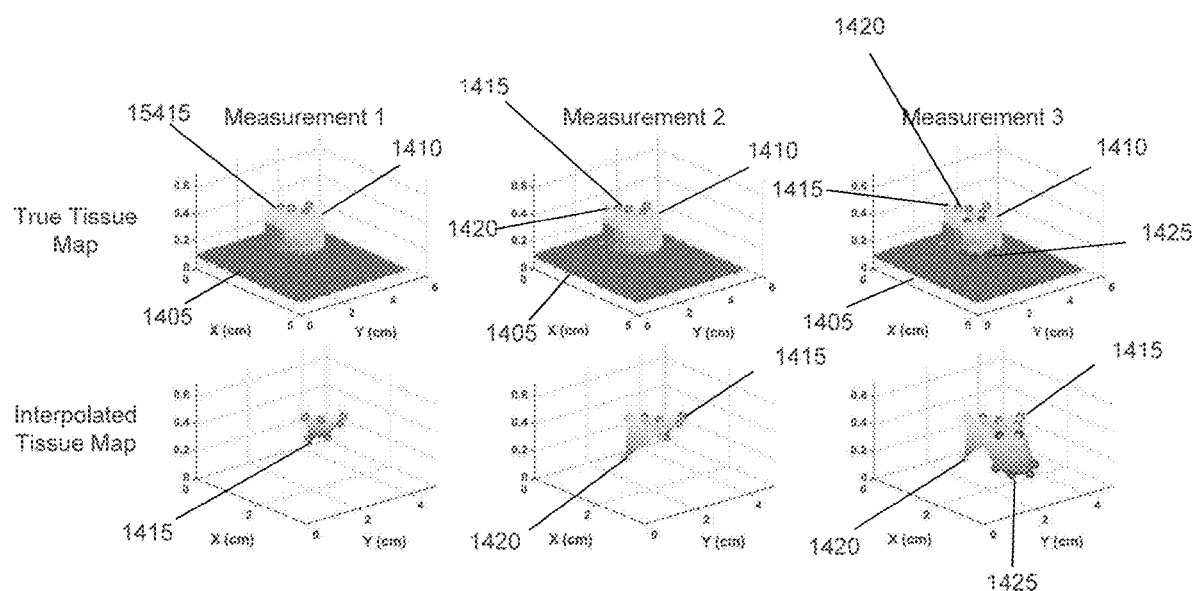
FIG. 14 is a set of exemplary graphs illustrating simulations of three measurements using the exemplary LASSP probe according to an exemplary embodiment of the present disclosure.

FIG. 14 shows a set of exemplary graphs illustrating simulations of three measurements using the exemplary LASSP probe according to an exemplary embodiment of the present disclosure. In particular, the simulation was performed for three measurements made using the LASSO probe head with 6 source-detector pairs arranged in a semi-circle. The simulated tissue being probed is shown in the first row. Healthy tissue (e.g., shown by areas 1405) can have an optical coefficient of 0.1 and ablated tissue (e.g., shown by areas 1410) can have a coefficient of 0.3. Gaussian noise can be added to simulated tissue environment (e.g., $\mu=0$, $\sigma=0.001$). The rings mark the location and coefficient measured by each of the probe's detectors, and can indicate when the measurement was made (e.g., rings 1415=meas. 1, rings 1420=meas. 2, rings 1425=meas. 3). The second row shows the tissue map being iteratively built by interpolating between all measurement sites.

Figure 15:
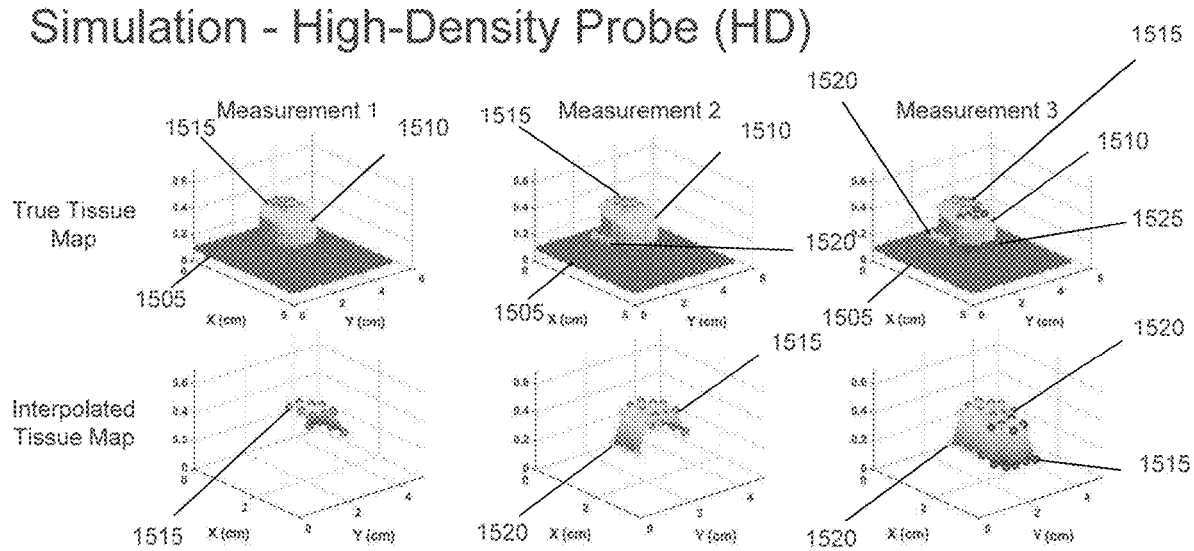
FIG. 15 is a set of exemplary graphs illustrating simulations of three measurements using a high-density probe head according to an exemplary embodiment of the present disclosure.

FIG. 15 shows a set of exemplary graphs illustrating simulations of three measurements using an HD probe head with 12 source-detector pairs (e.g., 3 columns four rows each) according to an exemplary embodiment of the present disclosure. The simulated tissue being probed is shown in the first row. Healthy tissue (e.g., areas 1505) can have an optical coefficient of 0.1 and ablated tissue (e.g., areas 1510) can have a coefficient of 0.3. Gaussian noise can be added to simulated tissue environment (e.g., $\mu=0$, $\sigma=0.001$). The rings mark the location and coefficient measured by each of the probe's detectors, and indicate when the measurement was made (e.g., rings 1515=meas. 1, rings 1520=meas. 2, rings 1525=meas. 3). The second row shows the tissue map being iteratively built by interpolating between all measurement sites.

Figure 16:
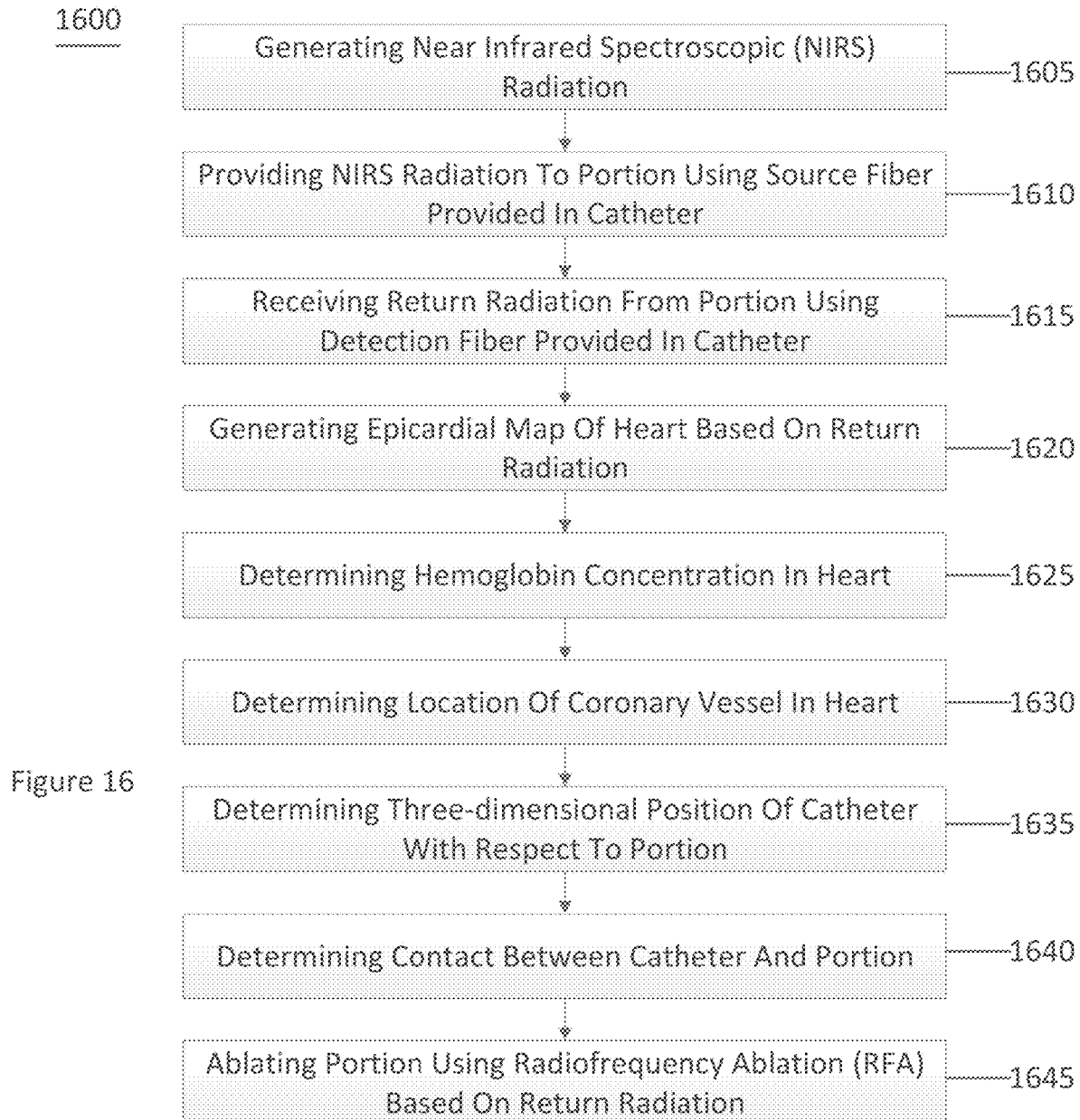
FIG. 16 is an exemplary flow diagram of a method for ablating a portion of a sample according to an exemplary embodiment of the present disclosure.

FIG. 16 shows an exemplary flow diagram of a method 1600 for ablating a portion of a sample according to an exemplary embodiment of the present disclosure. For example, at procedure 1605, near infrared spectroscopic (NIRS) radiation can be generated. At procedure 1610, the NIRS radiation can be provided to the portion using source fiber provided in a catheter. At procedure 1615, return radiation from the portion that is based on the NIRS radiation that was provided to the portion of the sample can be received using a detection fiber provided in the catheter. At procedure 1620, an epicardial map of the heart can be generated based on the return radiation. At procedure 1625, a hemoglobin concentration in the heart can be determined. At procedure 1630, a location of the coronary vessel in the heart can be determined. At procedure 1635, a three-dimensional position of the catheter can be determined with respect to the portion. At procedure 1640, a contact between the catheter and the portion can be determined. At r 1645, the portion can be ablated using a radiofrequency ablation (RFA) based on the return radiation.

Figure 17:
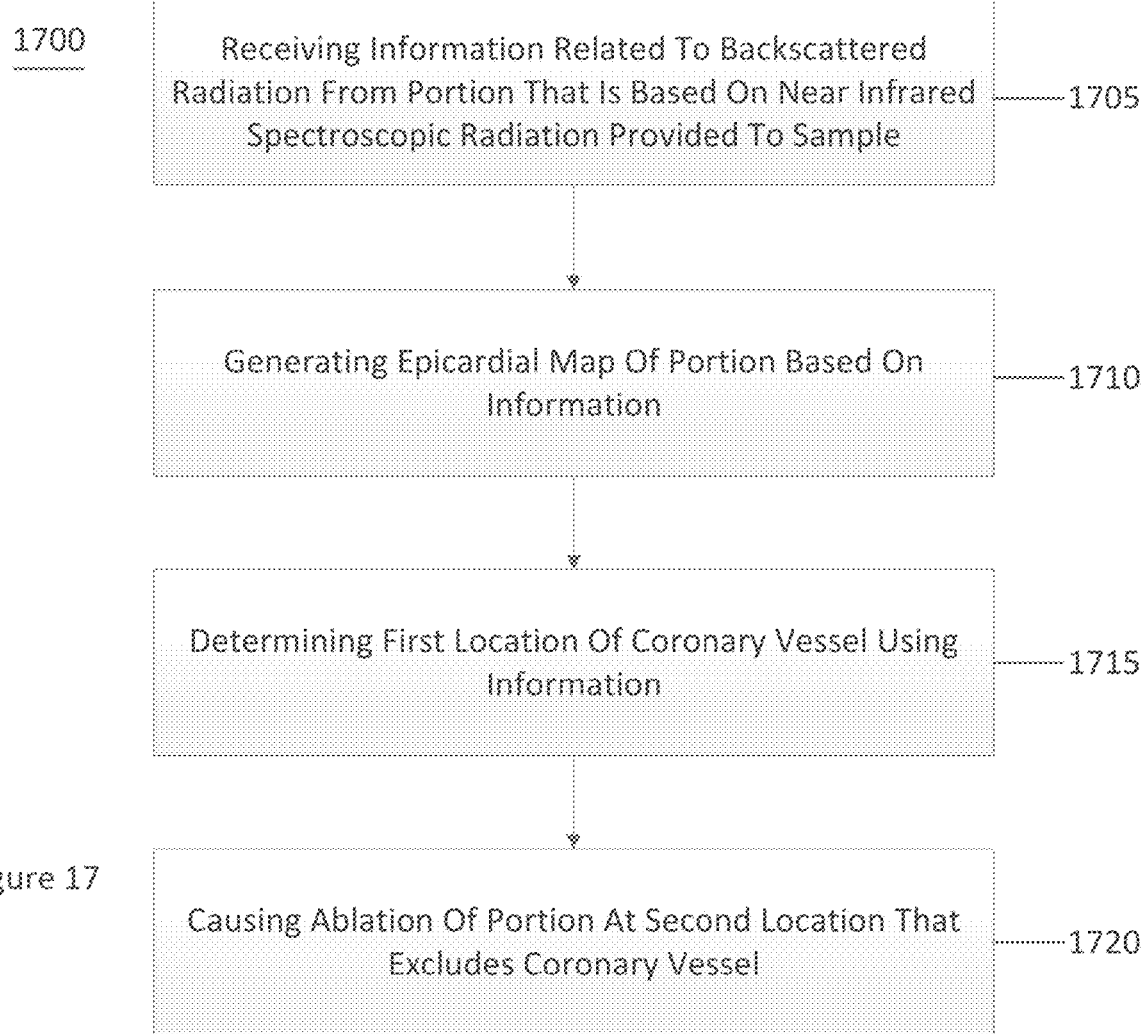
FIG. 17 is an exemplary flow diagram of a method for causing an ablation of a portion of a sample according to an exemplary embodiment of the present disclosure.

FIG. 17 shows an exemplary flow diagram of a method 1700 for causing an ablation of a portion of a sample according to an exemplary embodiment of the present disclosure. For example, at procedure 1705 information related to a backscattered radiation from the portion that is based on near infrared spectroscopic radiation provided to the sample can be received. At procedure 1710, an epicardial map of the portion can be generated based on the information. At procedure 1715, a first location of a coronary vessel can be determined using the information. At procedure 1720, the ablation of the portion can be caused at a second location that excludes the coronary vessel.

Figure 18:
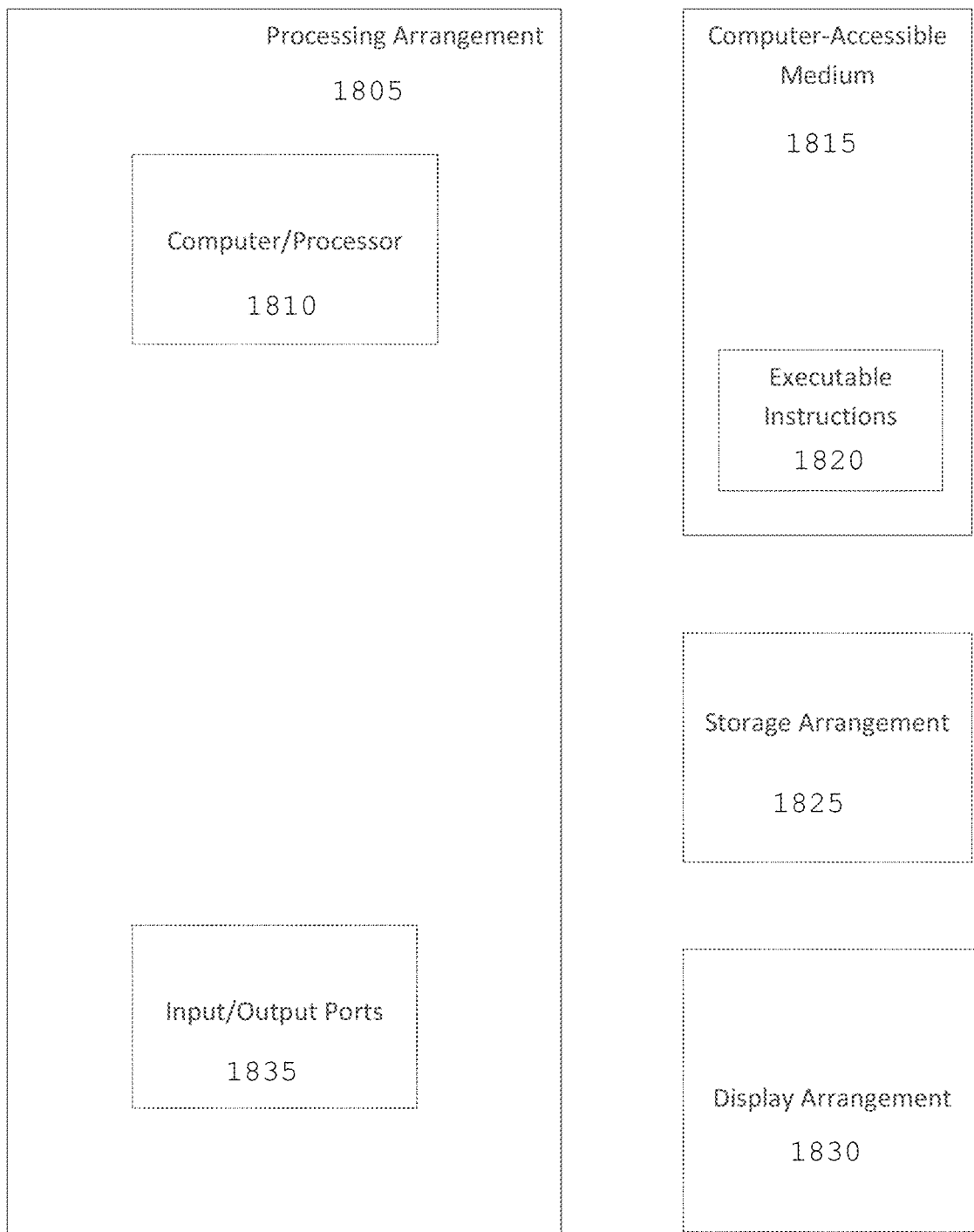
FIG. 18 is an illustration of an exemplary block diagram of an exemplary system in accordance with certain exemplary embodiments of the present disclosure.

FIG. 18 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 1805. Such processing/computing arrangement 1805 can be, for example entirely or a part of, or include, but not limited to, a computer/processor 1810 that can include, for example one or more microprocessors, and use instructions stored on a computer-accessible medium (e.g., RAM, ROM, hard drive, or other storage device).

As shown in FIG. 18, for example a computer-accessible medium 1815 (e.g., as described herein above, a storage device such as a hard disk, floppy disk, memory stick, CD-ROM, RAM, ROM, etc., or a collection thereof) can be provided (e.g., in communication with the processing arrangement 1805). The computer-accessible medium 1815 can contain executable instructions 1820 thereon. In addition, or alternatively, a storage arrangement 1825 can be provided separately from the computer-accessible medium 1815, which can provide the instructions to the processing arrangement 1805 so as to configure the processing arrangement to execute certain exemplary procedures, processes, and methods, as described herein above, for example.

Further, the exemplary processing arrangement 1805 can be provided with or include an input/output ports 1835, which can include, for example a wired network, a wireless network, the internet, an intranet, a data collection probe, a sensor, etc. As shown in FIG. 18, the exemplary processing arrangement 1805 can be in communication with an exemplary display arrangement 1830, which, according to certain exemplary embodiments of the present disclosure, can be a touch-screen configured for inputting information to the processing arrangement in addition to outputting information from the processing arrangement, for example. Further, the exemplary display arrangement 1830 and/or a storage arrangement 1825 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:
1. Sosa E, Scanavacca M, d'Avila A, Pilleggi F. A new technique to perform epicardial mapping in the electrophysiology laboratory. J Cardiovasc Electrophysiol June 1996; 7:531-536.
2. Soejima K, Stevenson W G, Sapp J L, Selwyn A P, Couper G, Epstein L M. Endocardial and epicardial radiofrequency ablation of ventricular tachycardia associated with dilated cardiomyopathy: the importance of low-voltage scars. Journal of the American College of Cardiology May 19, 2004; 43:1834-1842.
3. Dukkipati S R, d'Avila A, Soejima K, Bala R, Inada K, Singh S, Stevenson W G, Marchlinski F E, Reddy V Y. Long-term outcomes of combined epicardial and endocardial ablation of monomorphic ventricular tachycardia related to hypertrophic cardiomyopathy. Circ Arrhythm Electrophysiol April 2011; 4:185-194.
4. Stevenson W G, Wilber D J, Natale A, et al. Irrigated radiofrequency catheter ablation guided by electroanatomic mapping for recurrent ventricular tachycardia after myocardial infarction: the multicenter thermocool ventricular tachycardia ablation trial. Circulation Dec. 16, 2008; 118:2773-2782.
5. Sacher F, Tedrow U B, Field M E, Raymond J M, Koplan B A, Epstein L M, Stevenson W G. Ventricular tachycardia ablation: evolution of patients and procedures over 8 years. Circ Arrhythm Electrophysiol August 2008; 1:153-161.
6. Desjardins B, Morady F, Bogun F. Effect of epicardial fat on electroanatomical mapping and epicardial catheter ablation. Journal of the American College of Cardiology Oct. 12, 2010; 56:1320-1327.

Fleming C P, Quan K J, Rollins A M. Toward guidance of epicardial cardiac radiofrequency ablation therapy using optical coherence tomography. Journal of biomedical optics July-August 2010; 15:041510.

8. Fleming C P, Eckert J, Halpern E F, Gardecki J A, Tearney G J. Depth resolved detection of lipid using spectroscopic optical coherence tomography. Biomedical optics express 2013; 4:1269-1284.

9. d'Avila A, Houghtaling C, Gutierrez P, Vragovic O, Ruskin J N, Josephson M E, Reddy V Y. Catheter ablation of ventricular epicardial tissue: a comparison of standard and cooled-tip radiofrequency energy. Circulation May 18, 2004; 109:2363-2369.

10. Madder R D, Khan M, Husaini M, Chi M, Dionne S, VanOosterhout S, Borgman A, Collins J S, Jacoby M. Combined Near-Infrared Spectroscopy and Intravascular Ultrasound Imaging of Pre-Existing Coronary Artery Stents: Can Near-Infrared Spectroscopy Reliably Detect Neoatherosclerosis? Circulation Cardiovascular imaging January 2016; 9.

11. Fard A M, Vacas-Jacques P, Hamidi E, Wang H, Carruth R W, Gardecki J A, Tearney G J. Optical coherence tomography—near infrared spectroscopy system and catheter for intravascular imaging. Optics express Dec. 16, 2013; 21:30849-30858.

12. Singh-Moon R P, Yao X, Iyer V, Marboe C, Whang W, Hendon C P. Real-time optical spectroscopic monitoring of non-irrigated lesion progression within atrial and ventricular tissues. J Biophotonics Jul. 30, 2018e201800144.

13. Singh-Moon R P, Marboe C C, Hendon C. Near-infrared spectroscopy integrated catheter for characterization of myocardial tissues: preliminary demonstrations to radiofrequency ablation therapy for atrial fibrillation. Biomed Opt Express 2015; 6:2494-2511.

14. Nakamori S, Nezafat M, Ngo L H, Manning W J, Nezafat R. Left Atrial Epicardial Fat Volume Is Associated With Atrial Fibrillation: A Prospective Cardiovascular Magnetic Resonance 3D Dixon Study. Journal of the American Heart Association Mar. 23, 2018; 7.

15. De Coster T, Claus P, Seemann G, Willems R, Sipido K R, Panfilov A V. Myocyte Remodeling Due to Fibro-Fatty Infiltrations Influences Arrhythmogenicity. Front Physiol 2018; 9:1381.

16. De Coster T, Claus P, Kazbanov I V, Haemers P, Willems R, Sipido K R, Panfilov A V. Arrhythmogenicity of fibro-fatty infiltrations. Sci Rep Feb. 1, 2018; 8:2050.

17. Samanta R, Pouliopoulos J, Thiagalingam A, Kovoor P. Role of adipose tissue in the pathogenesis of cardiac arrhythmias. Heart rhythm: the official journal of the Heart Rhythm Society January 2016; 13:311-320.

18. Batal O, Schoenhagen P, Shao M, Ayyad A E, Van Wagoner D R, Halliburton S S, Tchou P J, Chung M K. Left atrial epicardial adiposity and atrial fibrillation. Circ Arrhythm Electrophysiol June 2010; 3:230-236.

19. Viles-Gonzalez J F, de Castro Miranda R, Scanavacca M, Sosa E, d'Avila A. Acute and chronic effects of epicardial radiofrequency applications delivered on epicardial coronary arteries. Circ Arrhythm Electrophysiol August 2011; 4:526-531.

20. A. N. Ganesan, N. J. Shipp, A. G. Brooks, P. Kuklik, D. H. Lau, H. S. Lim, T. Sullivan, K. C. Roberts-Thomson, and P. Sanders, "Long-term outcomes of catheter ablation of atrial fibrillation: a systematic review and meta-analysis," Journal of the American Heart Association 2, e004549 (2013).

21. M. A. Wood, "Exposing gaps in linear radiofrequency lesions: form before function," Circ Arrhythm Electrophysiol 4, 257-259 (2011).

22. C. P. Fleming, K. J. Quan, H. Wang, G. Amit, and A. M. Rollins, "In vitro characterization of cardiac radiofrequency ablation lesions using optical coherence tomography," Optics express 18, 3079-3092 (2010).

23. S. Iskander-Rizk, P. Kruizinga, A. F. W. van der Steen, and G. van Soest, "Spectroscopic photoacoustic imaging of radiofrequency ablation in the left atrium," Biomedical optics express 9, 1309-1322 (2018).

24. M. Mercader, L. Swift, S. Sood, H. Asfour, M. Kay, and N. Sarvazyan, "Use of endogenous NADH fluorescence for real-time in situ visualization of epicardial radiofrequency ablation lesions and gaps," American journal of physiology. Heart and circulatory physiology 302, H2131-2138 (2012).

25. R. P. Singh-Moon, X. Yao, V. Iyer, C. Marboe, W. Whang, and C. P. Hendon, "Real-time optical spectroscopic monitoring of non-irrigated lesion progression within atrial and ventricular tissues," J Biophotonics, e201800144 (2018).

26. J. Swartling, S. Palsson, P. Platonov, S. B. Olsson, and S. Andersson-Engels, "Changes in tissue optical properties due to radio-frequency ablation of myocardium," Medical & biological engineering & computing 41, 403-409 (2003).

What is claimed is:

1. A catheter comprising:
   at least one source fiber configured to (i) receive a near infrared spectroscopic (NIRS) radiation, and (ii) provide the NIRS radiation to at least one portion of at least one sample;
   at least one detection fiber configured to receive a return radiation from the at least one sample that is based on the NIRS radiation that was provided to the at least one portion of the at least one sample; and
   at least one ablation electrode configured to ablate the at least one sample based on the return radiation.

2. The catheter of claim 1, further comprising a single sheath, wherein the at least one source fiber, the at least one detection fiber, and the at least one ablation electrode are integrated into the single sheath within the catheter.

3. The catheter of claim 1, wherein the at least one ablation electrode is a radiofrequency ablation electrode.

4. The catheter of claim 1, wherein a configuration of the at least one source fiber and the at least one detection fiber are spaced apart at a specific distance from one another.

5. The catheter of claim 4, wherein the specific distance is between about 0 mm to about 4 mm.

6. The catheter of claim 1, further comprising at least one broadband light source configured to generate the NIRS radiation being received by the at least one source fiber.

7. The catheter of claim 1, further comprising at least one continuous-wave light source configured to generate the NIRS radiation being received by the at least one source fiber.

8. The catheter of claim 1, further comprising a charge coupled device configured to (i) receive the return radiation from the at least one detection fiber, and (ii) generate imaging information based on the return radiation, wherein the imaging information is associated with the at least one portion of the at least one sample.

9. The catheter of claim 1, wherein:
   the at least one source fiber includes at least six source fibers, the at least one detection fiber includes at least six detection fibers, and the at least one ablation electrode includes at least twelve ablation electrodes, and wherein a combination of the at least six source fibers and the at least six detection fibers facilitates a parallel or simultaneous detection of information regarding the at least one portion of the at least one sample.

10. The catheter of claim 9, wherein:
one of the at least six source fibers and one of the at least six detection fibers form a pair of fibers,
one of the at least twelve ablation electrodes is disposed on a first side of the pair of fibers,
another one of the at least twelve ablation electrodes is disposed on a second side of the pair of fibers, and
the first side is disposed opposite to the second side with respect to the pair of fibers.

11. A method for ablating at least one portion of at least one sample, comprising:
generating at least one near infrared spectroscopic (NIRS) radiation;
providing the at least one NIRS radiation to the at least one portion using at least one source fiber provided in a catheter;
receiving at least one return radiation from the at least one portion that is based on the at least one NIRS radiation that was provided to the at least one portion of the at least one sample using at least one detection fiber provided in the catheter; and
ablating the at least one portion using at least one ablation electrode provided in the catheter based on the at least one return radiation.

12. The method of claim 11, wherein the at least one ablation electrode includes at least one radiofrequency ablation (RFA) electrode integrated into the catheter.

13. The method of claim 11, further comprising determining a three-dimensional position of the catheter with respect to the at least one portion.

14. The method of claim 11, further comprising determining a contact between the catheter and the at least one portion.

15. The method of claim 11, wherein the at least one sample includes a heart, and further comprising generating at least one epicardial map of the heart based on the at least one return radiation.

16. The method of claim 15, wherein the at least one epicardial map includes at least one of (i) at least one coronary vessel in the heart, (ii) fat in the heart, (iii) scar tissue in the heart, or (iv) fibrosis in the heart.

17. The method of claim 16, further comprising determining a location of the at least one coronary vessel in the heart by determining a hemoglobin concentration in the heart.

18. The method of claim 17, further comprising determining the hemoglobin concentration using a spectral unmixing procedure.

19. The method of claim 18, wherein the spectral unmixing procedure is an inverse Monte Carlo procedure.

20. The method of claim 11, further comprising generating at least one optical substrate map of at least one portion of the at least one sample based on the at least one return radiation.

21. The method of claim 20, further comprising automatically assessing at least one substrate using the at least one optical substrate map, wherein the at least one substrate includes a pulmonary vein, a coronary artery, fat, fibrosis or a scar.

22. The method of claim 20, further comprising:
tracking a position of the catheter at or within the tissue; and
interpolating the at least one optical substrate map based on the at least one return radiation as a function of the tracked position.

23. The method of claim 20, wherein the generating of the at least one optical substrate map includes tracking at least one input.

24. The method of claim 11, wherein the at least one source fiber includes a plurality of source fibers, wherein the at least one detection fiber includes a plurality of detection fibers, and wherein the receiving of at least one return radiation includes a receipt of plurality of radiations, each from a respective one of the plurality of detection fibers, facilitating a parallel or simultaneous detection of information regarding the at least one portion of the at least one sample.

25. The method of claim 24, wherein the information is simultaneously detected from different locations on or in the at least one portion of the at least one sample.

26. The method of claim 11, wherein the source and detection fibers extend in the catheter for a majority of a length thereof.

27. A non-transitory computer-accessible medium having stored thereon computer-executable instructions for causing an ablation of at least one portion of at least one sample, wherein, when a computing arrangement executes the instructions, the computing arrangement is configured to perform procedures comprising:
receiving information related to a backscattered radiation from the at least one portion that is based on at least one near infrared spectroscopic radiation provided to the at least one sample by at least one source fiber provided in a catheter, wherein the received information is based on at least one return radiation at least one detection fiber provided in the catheter;
generating at least one epicardial map of the at least one portion based on the information;
determining a first location of at least one coronary vessel using the information; and
causing the ablation of the at least one portion by at least one ablation electrode provided in the catheter at a second location that excludes the at least one coronary vessel.

* * * * *